(12) United States Patent
Ram

(10) Patent No.: US 10,905,346 B2
(45) Date of Patent: *Feb. 2, 2021

(54) PSEUDO-CONDUCTIVE HIGH-ELECTRON MOBILITY TRANSISTORS AND MICROELECTRONIC SENSORS BASED ON THEM

(71) Applicant: EPITRONIC HOLDINGS PTE LTD., Singapore (SG)

(72) Inventor: Ayal Ram, Singapore (SG)

(73) Assignee: EPITRONIC HOLDINGS PTE LTD., Singapore (SG)

( * ) Notice: Subject to any disclaimer, the term of this patent is extended or adjusted under 35 U.S.C. 154(b) by 120 days.

This patent is subject to a terminal disclaimer.

(21) Appl. No.: 16/122,032

(22) Filed: Sep. 5, 2018

(65) Prior Publication Data

US 2019/0021622 A1  Jan. 24, 2019

Related U.S. Application Data

(63) Continuation-in-part of application No. PCT/IB2017/051319, filed on Mar. 7, 2017, which is
(Continued)

(51) Int. Cl.
*H01L 29/778* (2006.01)
*A61B 5/04* (2006.01)
(Continued)

(52) U.S. Cl.
CPC .......... *A61B 5/0408* (2013.01); *A61B 1/2736* (2013.01); *A61B 3/16* (2013.01);
(Continued)

(58) Field of Classification Search
CPC ................ H01L 29/778; H01L 29/7781–7786
(Continued)

(56) References Cited

U.S. PATENT DOCUMENTS 3,991,365 A * 11/1976 Takeuchi ................. A61B 8/02
324/76.22
7,547,939 B2 * 6/2009 Simin ............... H01L 29/41725
257/312
(Continued)

FOREIGN PATENT DOCUMENTS

EP       2799852 A1   11/2014

OTHER PUBLICATIONS

Vanko et al. "MEMS pressure sensor with an AlGaN/GaN based high electron mobility transistor" Tech Connect Briefs 2015. (Year: 2015).*
(Continued)

*Primary Examiner* — Joseph A Stoklosa
*Assistant Examiner* — Brian M Antiskay
(74) *Attorney, Agent, or Firm* — The Roy Gross Law Firm, LLC; Roy Gross

(57) ABSTRACT

In some embodiments, an open-gate pseudo-conductive high-electron mobility transistor (PC-HEMT) includes a multilayer hetero-junction structure made of III-V single-crystalline or polycrystalline semiconductor materials. This structure includes at least one buffer layer and a barrier layer, and is deposited on a substrate layer. The PC-HEMT further includes a two-dimensional electron gas (2DEG) or two-dimensional hole gas (2DHG) conducting channel formed at the interface between the buffer layer and the barrier layer, source and drain contacts, either ohmic or non-ohmic, connected to the 2DEG or 2DHG conducting channel, electrical metallizations for connecting the PC-HEMT to an electric circuit, and an open gate area between the source and drain contacts. Some embodiments use non-ohmic contacts, have thickness of the top (buffer or barrier) layer in the open gate area in the range of 5-9 nm, which corresponds to the pseudo-conducting current range between normally-on
(Continued)

and normally-off operation mode of the transistor, and have the roughness of the surface barrier layer in the range of about 0.2 nm or less.

21 Claims, 35 Drawing Sheets
(28 of 35 Drawing Sheet(s) Filed in Color)

Related U.S. Application Data a continuation of application No. 15/067,093, filed on Mar. 10, 2016, now abandoned, and a continuation of application No. 15/157,285, filed on May 17, 2016, now abandoned.

(60) Provisional application No. 62/384,831, filed on Sep. 8, 2016.

(51) Int. Cl.
| | | |
|---|---|---|
| *A61B 5/0408* | (2006.01) | |
| *H01L 29/205* | (2006.01) | |
| *H01L 29/20* | (2006.01) | |
| *A61B 5/00* | (2006.01) | |
| *A61B 5/0452* | (2006.01) | |
| *A61B 3/16* | (2006.01) | |
| *A61B 1/273* | (2006.01) | |
| *A61B 5/0478* | (2006.01) | |
| *A61B 7/04* | (2006.01) | |
| *G01N 27/414* | (2006.01) | |
| *A61B 5/08* | (2006.01) | |
| *A61B 5/11* | (2006.01) | |
| *A61B 5/021* | (2006.01) | |
| *A61B 5/05* | (2021.01) | |

(52) U.S. Cl.
CPC ........ *A61B 5/0006* (2013.01); *A61B 5/04017* (2013.01); *A61B 5/0452* (2013.01); *A61B 5/0478* (2013.01); *A61B 7/045* (2013.01); *G01N 27/414* (2013.01); *H01L 29/2003* (2013.01); *H01L 29/205* (2013.01); *H01L 29/7786* (2013.01); *A61B 5/002* (2013.01); *A61B 5/021* (2013.01); *A61B 5/05* (2013.01); *A61B 5/08* (2013.01); *A61B 5/1102* (2013.01); *A61B 5/1107* (2013.01); *A61B 5/681* (2013.01); *A61B 5/7225* (2013.01); *A61B 2562/164* (2013.01)

(58) Field of Classification Search
USPC .................................................. 257/194–195
See application file for complete search history.

(56) References Cited

U.S. PATENT DOCUMENTS

| | | | | |
|---|---|---|---|---|
| 2004/0144991 A1* | 7/2004 | Kikkawa | ........... | H01L 29/66462 257/103 |
| 2004/0262636 A1* | 12/2004 | Yang | ...... | B82Y 10/00 257/200 |
| 2005/0087766 A1 | 4/2005 | Kikkawa | | |
| 2008/0265258 A1* | 10/2008 | Tanabe | ................ | H01L 29/7787 257/76 |
| 2009/0072272 A1* | 3/2009 | Suh | ...... | H01L 29/1066 257/194 |
| 2011/0199102 A1* | 8/2011 | Garcia | ............... | G01N 27/4148 324/658 |
| 2011/0213271 A1* | 9/2011 | Telfort | ................... | A61B 7/003 600/586 |
| 2014/0203797 A1* | 7/2014 | Stivoric | ................... | F24F 11/30 324/76.11 |
| 2014/0323895 A1* | 10/2014 | Vitushinsky | ......... | A61B 5/0408 600/523 |
| 2015/0002135 A1* | 1/2015 | Moyer | ................... | G01R 19/14 324/119 |
| 2016/0064600 A1* | 3/2016 | Kuroda | ............... | H01L 29/7786 257/13 |
| 2017/0294528 A1* | 10/2017 | Ren | ...... | H01L 29/0657 |

OTHER PUBLICATIONS

Gassoumi et al. "Effect of surface passivation by Si N/SiO2 of AlGaN/GaN high-electron mobility transistors on Si substrate by deep level transient spectroscopy method" Semiconductor Physics and Technology (translated), 2013, vol. 47, Issue 7 2013. (Year: 2013).*
Corekci et al. "Surface Morphology of Al0.3Ga0.7N/Al2O3-High Electron Mobility Transistor Structure" Journal of Nanoscience and Nanotechnology, vol. 8 Issue: 2 pp. 640-644, Feb. 2008. (Year: 2008).*
Offermans et al; "Suspended AlGaN/GaN membrane devices with recessed open gate areas for ultra-low-power air duality monitoring" 2015 IEEE International Electron Devices Meeting (IEDM). Dec. 7, 2015, pp. 33.6.1-33.6.4.
International Search Report, PCT/IB2017/051319, Completed Jun. 21, 2017; dated Aug. 25, 2017, 6 pages.
Wrtten Opinion of the International Searching Authority, PCT/IB2017/051319, dated Aug. 25, 2017, 11 pages.

* cited by examiner $V_G \gg V_T$ $V_G = 0$
$V_G > V_T$ $V_G \ll V_T$

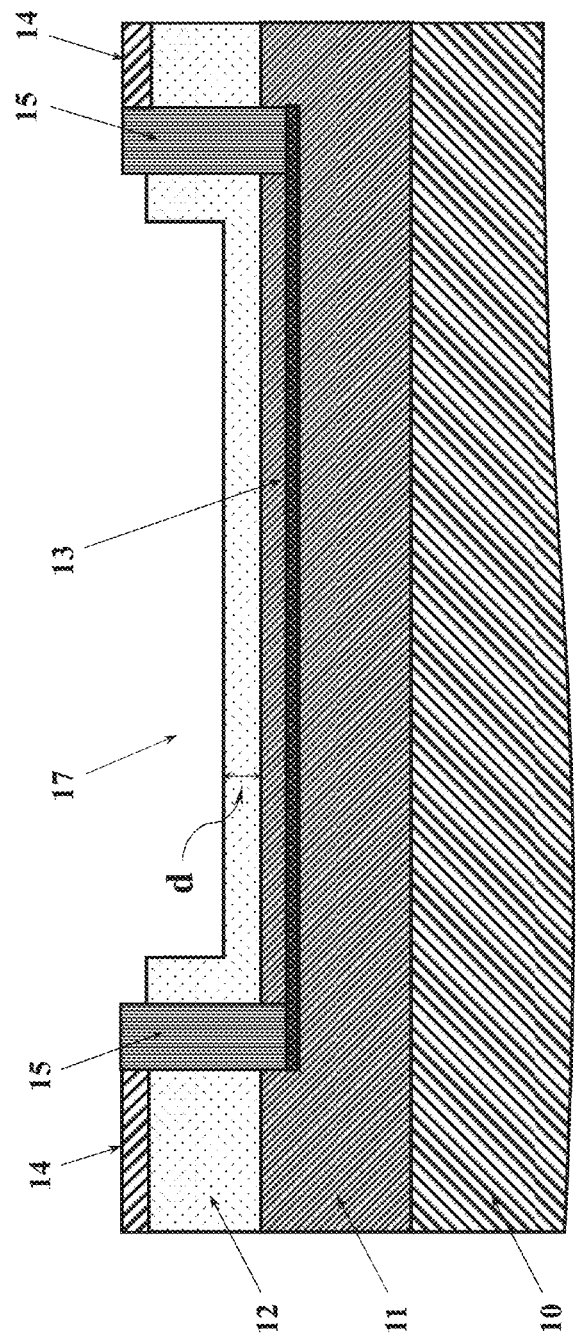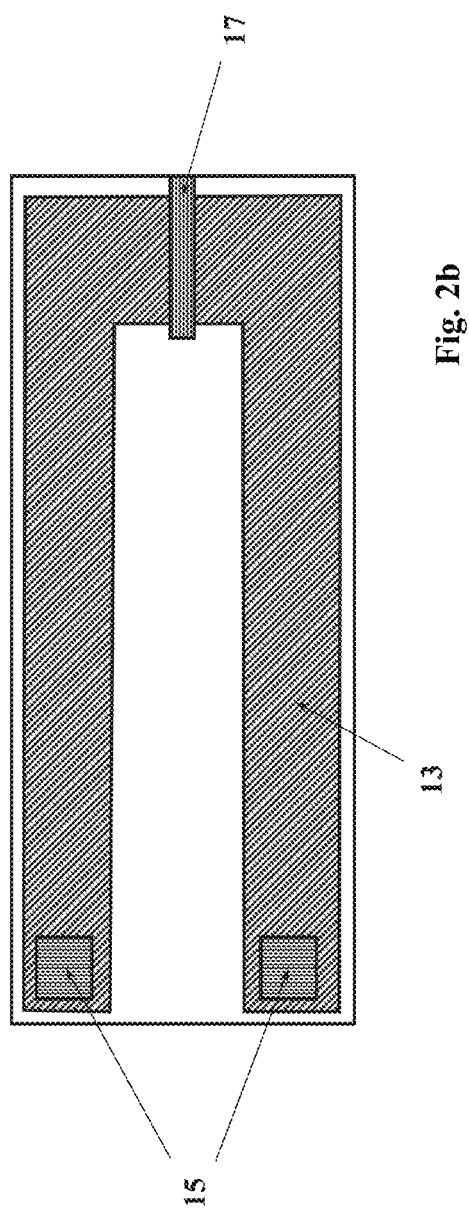

Best possible resolution at MA6 hard contact with AZ4533 is 2 μm

Alignment precision on 25 x 25 mm² samples is ± 2 μm

200 μm

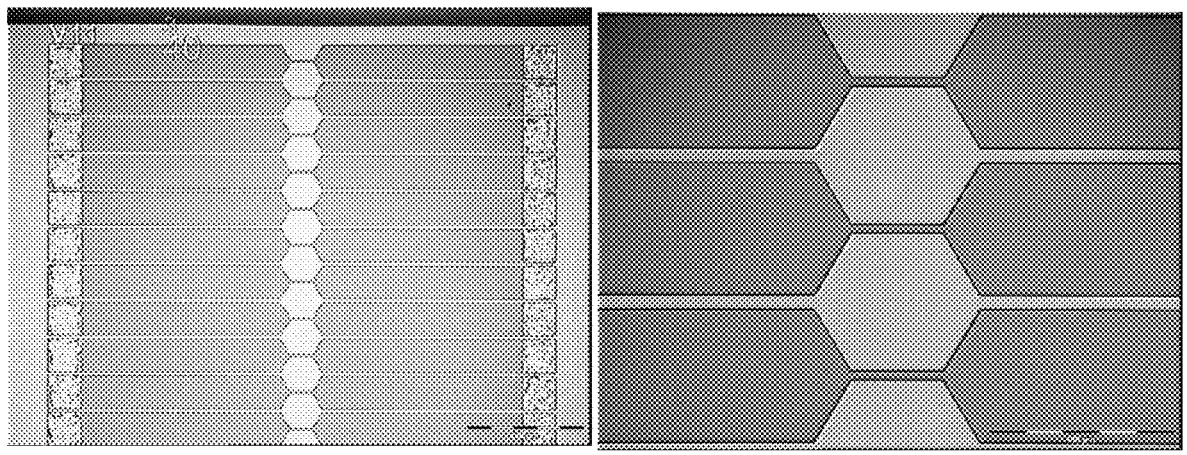
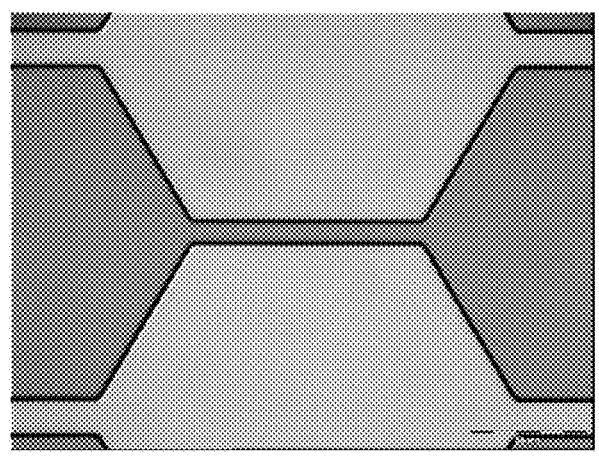
Fig. 5g

AZ4533 after development, prepared for ion implantation
2DEG channels (dark) patterned by ion-implantation after the resist removal
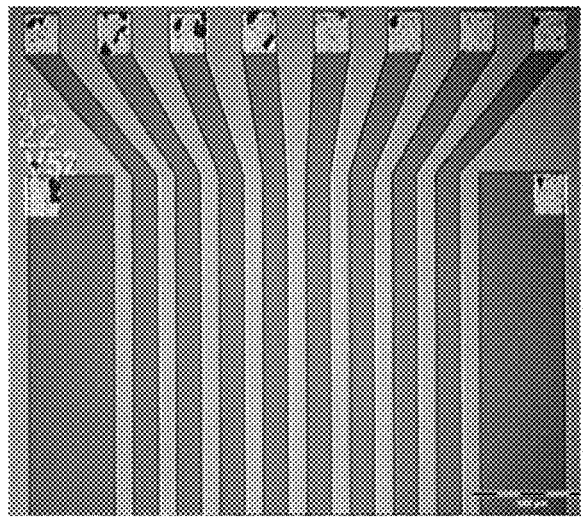
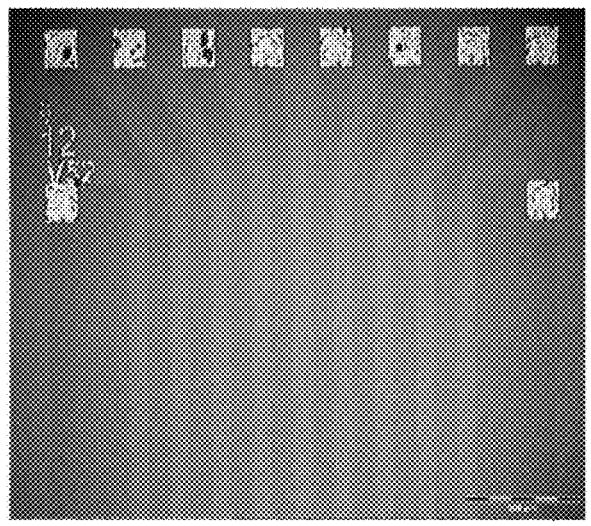
Fig. 5i
Fig. 5j
Fig. 5k
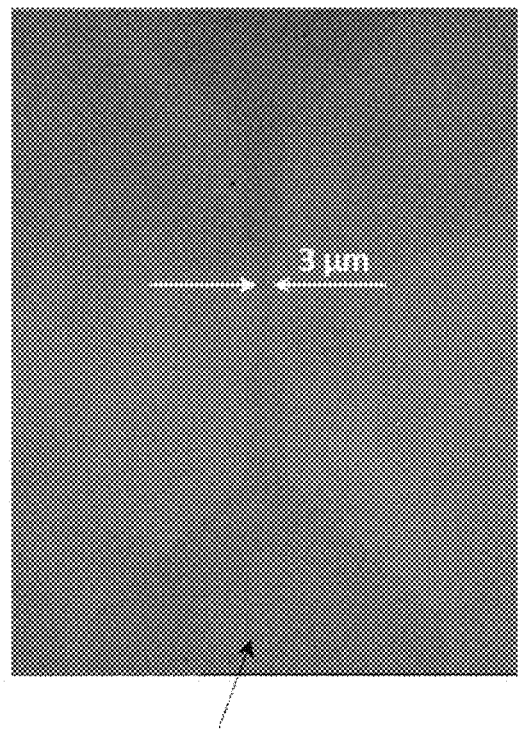
Visible non-implanted area (in dark) containing the conductive 2DEG channel Fig. 6a  Ga-Face Polarity
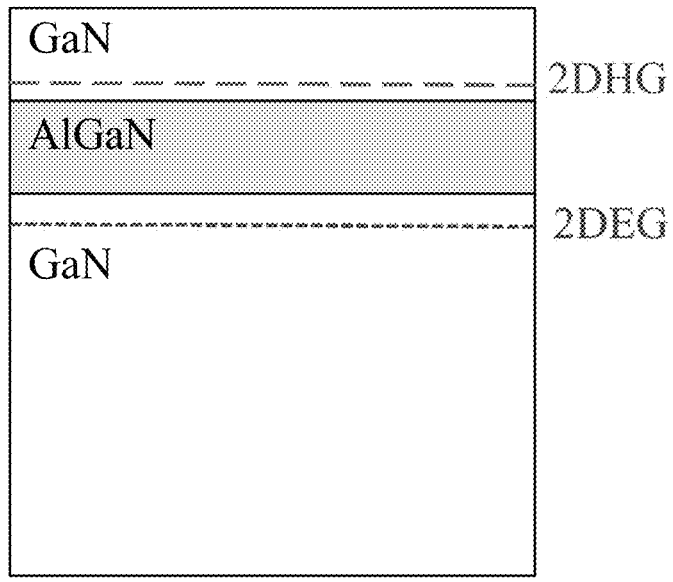
Fig. 6b  N-Face Polarity
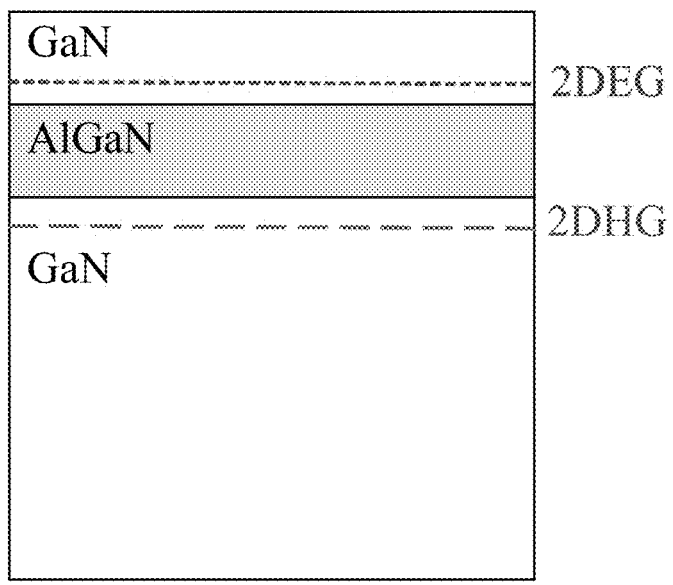

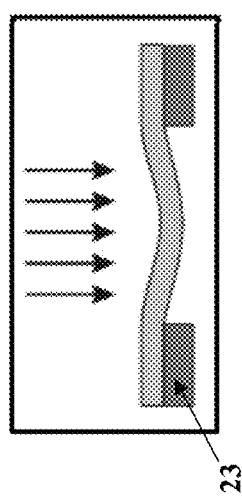
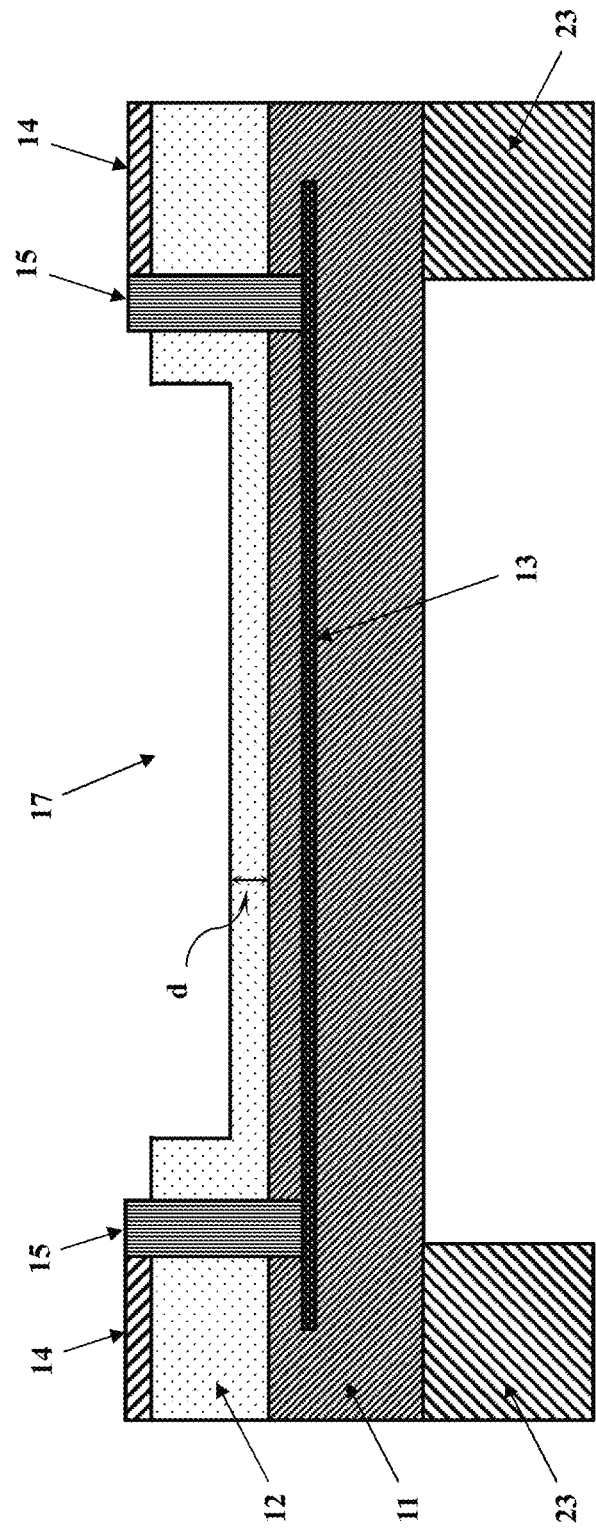
Fig. 11b
Fig. 11a

PSEUDO-CONDUCTIVE HIGH-ELECTRON MOBILITY TRANSISTORS AND MICROELECTRONIC SENSORS BASED ON THEM

RELATED APPLICATIONS

This application is a Continuation-In-Part of PCT Patent Application No. PCT/IB2017/051319 having International filing date of Mar. 7, 2017, which claims the benefit of priority of U.S. patent application Ser. No. 15/067,093 filed on Mar. 10, 2016, U.S. patent application Ser. No. 15/157,285 filed on May 17, 2016, and U.S. Provisional Application No. 62/384,831 filed on Sep. 8, 2016. The contents of the above applications are all incorporated by reference as if fully set forth herein in their entirety.

TECHNICAL FIELD

The present application relates to the field of microelectronic sensors based on high-electron-mobility transistors.

BACKGROUND

The polarization doped high-electron-mobility transistor (HEMT) is a field effect transistor (FET) in which two layers of different bandgap and polarisation field are grown upon each other forming a hetero-junction structure. As a consequence of the discontinuity in the polarisation field, surface charges are created at the interface between the layers of the hetero-junction structure. If the induced surface charge is positive, electrons will tend to compensate the induced charge resulting in the formation of the channel. Since in the HEMT, the channel electrons are confined in a quantum well in an infinitely narrow spatial region at the interface between the layers, these electrons are referred to as a two-dimensional electron gas (2DEG). This special confinement of the channel electrons in the quantum well actually grants them two-dimensional features, which strongly enhance their mobility surpassing the bulk mobility of the material in which the electrons are flowing.

The HEMTs based on the layers of III-V semiconductor materials, such as gallium nitride (GaN) and aluminium gallium nitride (AlGaN), have recently been developed with a view to high-voltage and high-power switching applications. The high voltages and high switching speeds allow smaller, more efficient devices, such as home appliances, communications and automobiles to be manufactured. To control the density of electrons in the 2DEG channel and to switch the HEMT on and off, the voltage at the gate of the transistor should be regulated.

FIGS. 1a-1c schematically shows the quantum well at three different biasing conditions starting from the positive gate potential ($V_G$), much higher than the threshold voltage ($V_T$), and going down to the 0V gate potential and further to the negative values below the threshold voltage. The $V_T$ is defined as a voltage required to populate electrons at the interface between the GaN and AlGaN layers, thereby creating conductivity of the 2DEG channel. Since the 2DEG channel electrons occupy energy levels below the Fermi level, the Fermi level in a quantum well is located above several energy levels when $V_G \gg V_T$ (FIG. 1a). This enables high population of the 2DEG channel electrons and hence, high conductivity. The HEMT is turned on in this case. However, when $V_G$ decreases to 0V (FIG. 1b), the Fermi level also drops with respect to the quantum well. As a result, much fewer electron energy levels are populated and the amount of the 2DEG channel electrons significantly decreases. When $V_G \ll V_T$ (FIG. 1c), all electron energy levels are above the Fermi level, and there is no 2DEG electrons below the gate. This situation is called "channel depletion", and the HEMT is turned off.

Many commercially available AlGaN/GaN-based HEMT structures have a negative $V_T$, resulting in a "normally-on" operation mode at 0V gate potential. They are called "depletion-mode transistors" and used in various power switching applications when the negative voltage must be applied on the gate in order to block the current. However, for safe operation at high voltage or high power density, in order to reduce the circuit complexity and eliminate standby power consumption, HEMTs with "normally-off" characteristics are preferred.

Several techniques to manufacture the normally-off HEMTs have been reported. Burnham et al (2010) proposed normally-off structures of the recessed gate type. In this structure, the AlGaN barrier layer is etched and the gate is brought closer to the interface between the AlGaN barrier layer and the GaN buffer layer. As the gate approaches the interface between the layers, the $V_T$ increases. The normally-off operation of the transistor is achieved once the depletion region reaches the interface and depletes the 2DEG channel at zero gate voltage. The major advantages of these HEMTs are relatively lower power consumption, lower noise and simpler drive circuits. These HEMTs are currently used, for example, in microwave and millimetre wave communications, imaging and radars.

Chang et al (2009) proposed instead of etching the relatively thick barrier layer to approach the AlGaN/GaN interface, to use a very thin AlGaN barrier. This structure also achieves normally-off operation by approaching the gate towards the AlGaN/GaN interface. Chen et al (2010) proposed to use the fluorine-based plasma treatment method. Although many publications have adopted various methods to achieve normally-off devices with minimum impact on the drain current, they unfortunately sacrificed device turn-on performance.

SUMMARY

The present application describes embodiments of a microelectronic sensor based on an open-gate pseudo-conductive high-electron mobility transistor (PC-HEMT). In some embodiments, a transistor comprises a substrate, on which a multilayer hetero-junction structure is deposited. In other embodiments, the multilayer hetero-junction structure is placed on free-standing membranes. This hetero-junction structure may comprise at least two layers, a buffer layer and a barrier layer, which are grown from III-V single-crystalline or polycrystalline semiconductor materials.

A conducting channel comprising a two-dimensional electron gas (2DEG), in case of two-layers configuration, or a two-dimensional hole gas (2DHG), in case of three-layers configuration, is formed at the interface between the buffer and barrier layers and provides electron or hole current in the system between source and drain electrodes. The source and drain, either ohmic or capacitively-coupled (non-ohmic) contacts are connected to the formed 2DEG/2DHG channel and to electrical metallizations, the latter are placed on top of the transistor and connect it to the sensor system. An optional dielectric layer is deposited on top of the hetero-junction structure. The open gate area of the transistor is formed between the source and drain areas as a result of recessing or growing of the top layer to a specific thickness.

If the source and drain contacts are non-ohmic (capacitively-coupled), in order to electrically contact the 2DEG/2DHG channel underneath, which is about 5-20 nm bellow metallizations, the AC-frequency regime is used. The capacitive coupling of the non-ohmic metal contacts with the 2DEG/2DHG channel is normally induced at the frequency higher than 30 kHz. In the case of non-ohmic contacts, the DC readout cannot be carried out. Instead, the AC readout or impedance measurements of the electric current flowing through the 2DEG/2DHG-channel are performed.

In some embodiments, the significant features of the PC-HEMT structure are that:
(i) the thickness of the top layer in the open gate area between the source and drain contacts is 5-9 nm, preferably 6-7 nm, more preferably 6.3 nm, and that corresponds to the pseudo-conducting current range between normally-on and normally-off operation mode of the transistor,
(ii) the surface of the top layer within the open gate area between the source and drain contacts has a roughness of about 0.2 nm or less, preferably 0.1 nm or less, more preferably 0.05 nm, and
(iii) the non-ohmic source and drain contacts for the capacitive coupling with the conductive 2DEG/2DHG channel optionally replace the ohmic contacts.

In some embodiments, the PC-HEMT multilayer heterojunction structure of the present application is grown from any available III-V single-crystalline or polycrystalline semiconductor materials, such as GaN/AlGaN, GaN/AlN, GaN/InN, GaN/InAlGaN, GaAs/AlGaAs GaN/InAlN, InN/InAlN, and $LaAlO_3/SrTiO_3$. In case of the GaN/AlGaN PC-HEMT, it has been surprisingly found that in the open gate area of this particular transistor, the thickness of the top layer that corresponds to the pseudo-conducting current range between normally-on and normally-off operation mode of the PC-HEMT, is about 6-7 nm.

In a particular embodiment, the hetero-junction structure may be a three-layer structure consisting of two buffer layers and one barrier layer squeezed between said buffer layers like in a sandwich. This may lead to formation of the two-dimensional hole gas (2DHG) in the top buffer layer above the barrier layer which results in reversing polarity of the transistor.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Disclosed embodiments will be understood and appreciated more fully from the following detailed description taken in conjunction with the appended figures.

FIG. 1a: positive gate potential ($+V_G$) is much higher than threshold voltage ($V_T$), FIG. 1b: 0V gate potential, and FIG. 1c: negative gate potential ($-V_G$) is below threshold voltage ($V_T$).

FIGS. 2a-2b schematically shows a cross-sectional view (XZ) (a) and a top view (XY) (b) of the PC-HEMT of an embodiment without a dielectric layer.

FIG. 5g shows the lithographic images of the multichannel samples.

FIG. 5i shows the lithographic image of the sensor layout with the AZ4533 resist after development, prepared for ion implantation.

FIG. 5j shows the 2DEG channels (dark) patterned by ion-implantation after the resist removal.

FIG. 5k shows the visible non-implanted area containing the conductive 2DEG channel.

FIG. 6a schematically shows the formation of the 2DEG and 2DHG conducting channels in the Ga-face three-layer Ga/AlGaN/GaN PC-HEMT structure.

FIG. 6b schematically shows the formation of the 2DEG and 2DHG conducting channels in the N-face three-layer GaN/AlGaN/GaN PC-HEMT structure.

FIG. 11a schematically shows a cross-sectional view of the PC-HEMT of an embodiment with free-standing membranes.

FIG. 11b illustrates a situation when the external pressure (mass effect) is applied on the sensor incorporating the PC-HEMT of FIG. 11a, and transferred into a changed internal strain caused by bending.

DETAILED DESCRIPTION

Figure 1A:
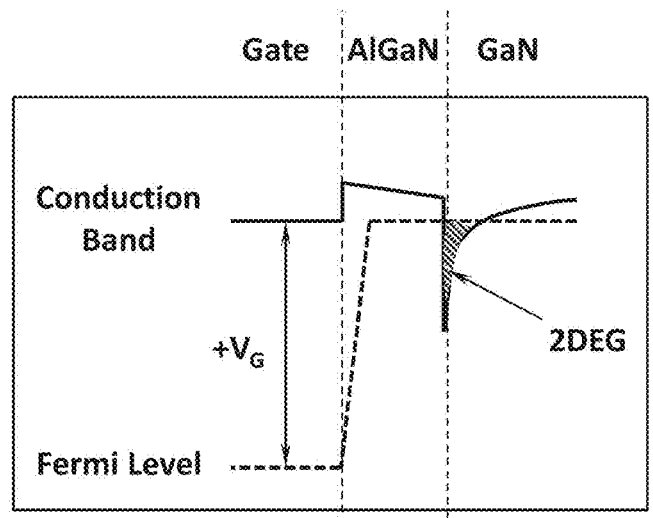
FIGS. 1a-1c schematically shows the quantum well at three different biasing conditions.
Figure 1B:
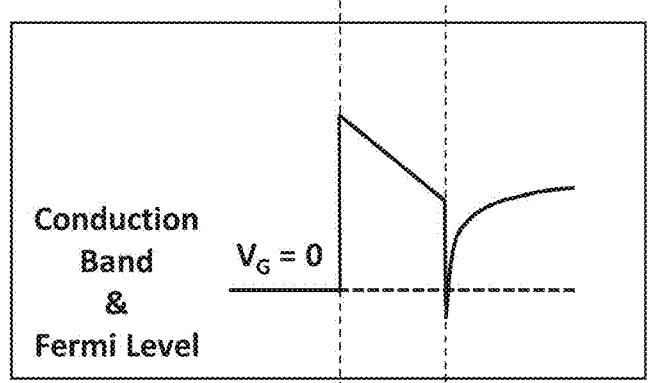
Figure 1C:
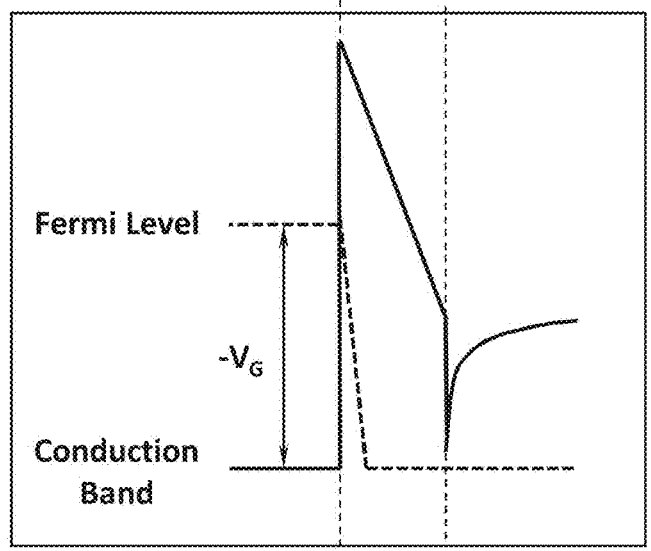

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising x and z" should not be limited to devices consisting only of components x and z. As used herein, the term "about" means there is a 10% tolerance of the mentioned or claimed value. As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached to", "connected to", "coupled with", "contacting", etc., another element, it can be directly on, attached to, connected to, coupled with or contacting the other element or intervening elements may also be present. In contrast, when an element is referred to as being, for example, "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

In one aspect of the disclosure, the present application describes an open-gate pseudo-conductive high-electron mobility transistor (PC-HEMT) comprising:
- a multilayer hetero-junction structure made of III-V single-crystalline or polycrystalline semiconductor materials, said structure comprising at least one buffer layer and at least one barrier layer, said layers being stacked alternately, and said structure being deposited on a substrate layer;
- a conducting channel comprising a two-dimensional electron gas (2DEG) or a two-dimensional hole gas (2DHG), formed at the interface between said buffer layer and said barrier layer and providing electron or hole current, respectively, in said transistor between source and drain contacts;
- the source and drain contacts connected to said 2DEG or 2DHG conducting channel and to electrical metallizations for connecting said transistor to an electric circuit; and
- an open gate area between said source and drain contacts;

wherein:
(i) the thickness (d) of a top layer (barrier or buffer) of said structure in said open gate area is 5-9 nm which corresponds to the pseudo-conducting current range between normally-on and normally-off operation mode of the transistor, and (ii) the surface of said top layer has a roughness of about 0.2 nm or less.

The source and drain contacts connecting the PC-HEMT to the electric circuit may be ohmic or non-ohmic (capacitively-coupled, as will be described below). In one embodiment, FIGS. 2a-2b shows a cross-sectional view (XZ) (a) and a top view (XY) (b) of the PC-HEMT of the present application comprising:

a multilayer hetero-junction structure made of III-V single-crystalline or polycrystalline semiconductor materials, said structure comprising one buffer layer (11) and one top barrier layer (12), and being deposited on a substrate layer (10);

a two-dimensional electron gas (2DEG) conducting channel (13) formed at the interface between said buffer layer (11) and said top barrier layer (12);

source and drain ohmic contacts (15) connected to said 2DEG conducting channel (13) and to electrical metallizations (14) for connecting said transistor to an electric circuit; and an open gate area (17) between said source and drain ohmic contacts (15);

wherein:

(i) the thickness (d) of said barrier layer (12) in said open gate area (17) is 5-9 nm which corresponds to the pseudo-conducting current range between normally-on and normally-off operation mode of the transistor, and (ii) the surface of said top barrier layer (12) has a roughness of about 0.2 nm or less.

Figure 2C:
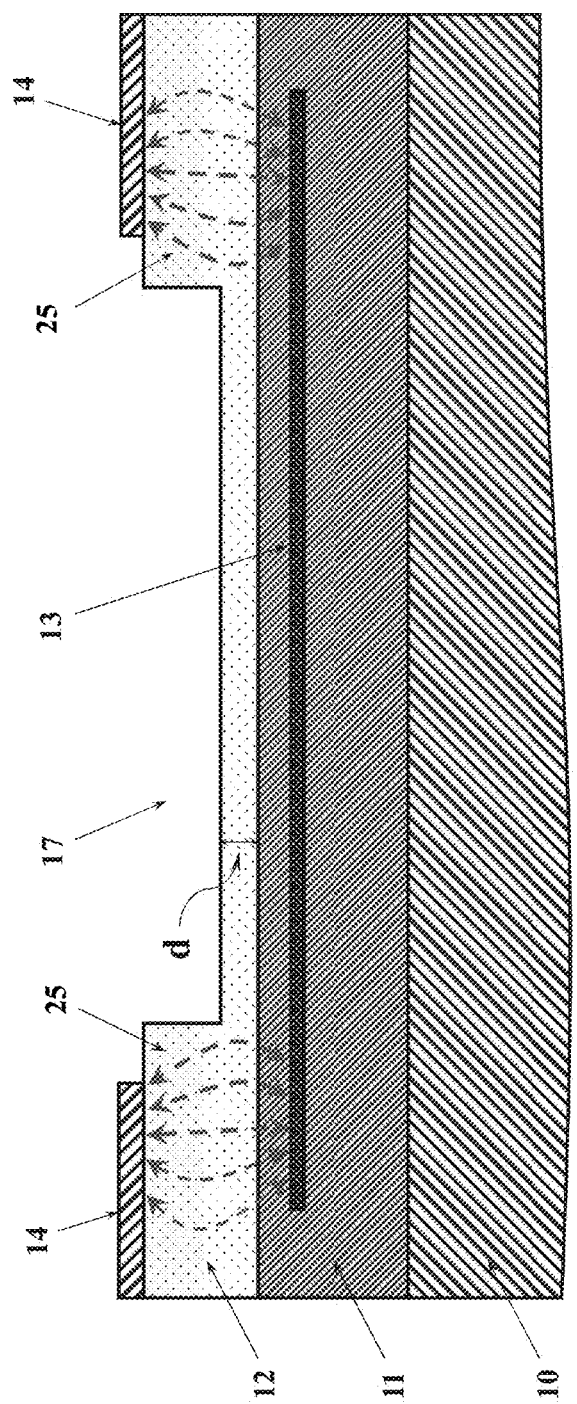
FIG. 2c schematically shows a cross-sectional view of the PC-HEMT of an embodiment having non-ohmic (capacitively-coupled) contacts and no dielectric layer.

Further, FIG. 2c shows a cross-sectional view of the PC-HEMT of another embodiment comprising:

a multilayer hetero-junction structure made of III-V single-crystalline or polycrystalline semiconductor materials, said structure comprising one buffer layer (11) and one top barrier layer (12), and being deposited on a substrate layer (10);

a two-dimensional electron gas (2DEG) conducting channel (13) formed at the interface between said buffer layer (11) and said top barrier layer (12);

electrical metallizations (14) capacitively-coupled to said 2DEG channel (13) for inducing displacement currents (25), thereby creating non-ohmic source and drain contacts connecting said transistor to an electric circuit; and an open gate area (17) between said source and drain non-ohmic contacts;

wherein:

(i) the thickness of the top barrier layer (12) in the open gate area (17) is 5-9 nm which corresponds to the pseudo-conducting current range between normally-on and normally-off operation mode of the transistor, and (ii) the surface of the top barrier layer (12) has a roughness of about 0.2 nm or less.

"Capacitive coupling" is defined as an energy transfer within the same electric circuit or between different electric circuits by means of displacement currents induced by existing electric fields between circuit/s nodes. In general, ohmic contacts are the contacts that follow Ohm's law, meaning that the current flowing through them is directly proportional to the voltage. Non-ohmic contacts however do not follow the same linear relationship of the Ohm's law. In other words, electric current passing through non-ohmic contacts is not linearly proportional to voltage. Instead, it gives a steep curve with an increasing gradient, since the resistance in that case increases as the electric current increases, resulting in increase of the voltage across non-ohmic contacts. This is because electrons carry more energy, and when they collide with atoms in the conducting channel, they transfer more energy creating new high-energy vibrational states, thereby increasing resistance and temperature.

When electrical metallizations are placed over single-crystalline or polycrystalline semiconductor material, the "Schottky contact" or "Schottky barrier contact" between the metal and the semiconductor occurs. Energy of this contact is covered by the Schottky-Mott rule, which predicts the energy barrier between a metal and a semiconductor to be proportional to the difference of the metal-vacuum work function and the semiconductor-vacuum electron affinity. However, this is an ideal theoretical behaviour, while in reality most interfaces between a metal and a semiconductor follow this rule only to some degree. The boundary of a semiconductor crystal abrupt by a metal creates new electron states within its band gap. These new electron states induced by a metal and their occupation push the centre of the band gap to the Fermi level. This phenomenon of shifting the centre of the band gap to the Fermi level as a result of a metal-semiconductor contact is defined as "Fermi level pinning", which differs from one semiconductor to another. If the Fermi level is energetically far from the band edge, the Schottky contact would preferably be formed. However, if the Fermi level is close to the band edge, an ohmic contact would preferably be formed. The Schottky barrier contact is a rectifying non-ohmic contact, which in reality is almost independent of the semi-conductor or metal work functions.

Thus, a non-ohmic contact allows electric current to flow only in one direction with a non-linear current-voltage curve that looks like that of a diode. On the contrary, an ohmic contact allows electric current to flow in both directions roughly equally within normal device operation range, with an almost linear current-voltage relationship that comes close to that of a resistor (hence, "ohmic").

FIG. 2c illustrates the situation when an electrical connection of the transistor to the 2DEG channel is realised via capacitive coupling to the electrical metallizations through a Schottky barrier contact. This coupling becomes possible only if sufficiently high AC frequency, higher than 30 kHz, is applied to the metallizations. The electrical metallizations capacitively coupled to the 2DEG channel utilise the known phenomenon of energy transfer by displacement currents. These displacement currents are induced by existing electrical fields between the electrical metallizations and the 2DEG conducting channel operated in the AC frequency mode through the Schottky contact as explained above.

Figure 2D:
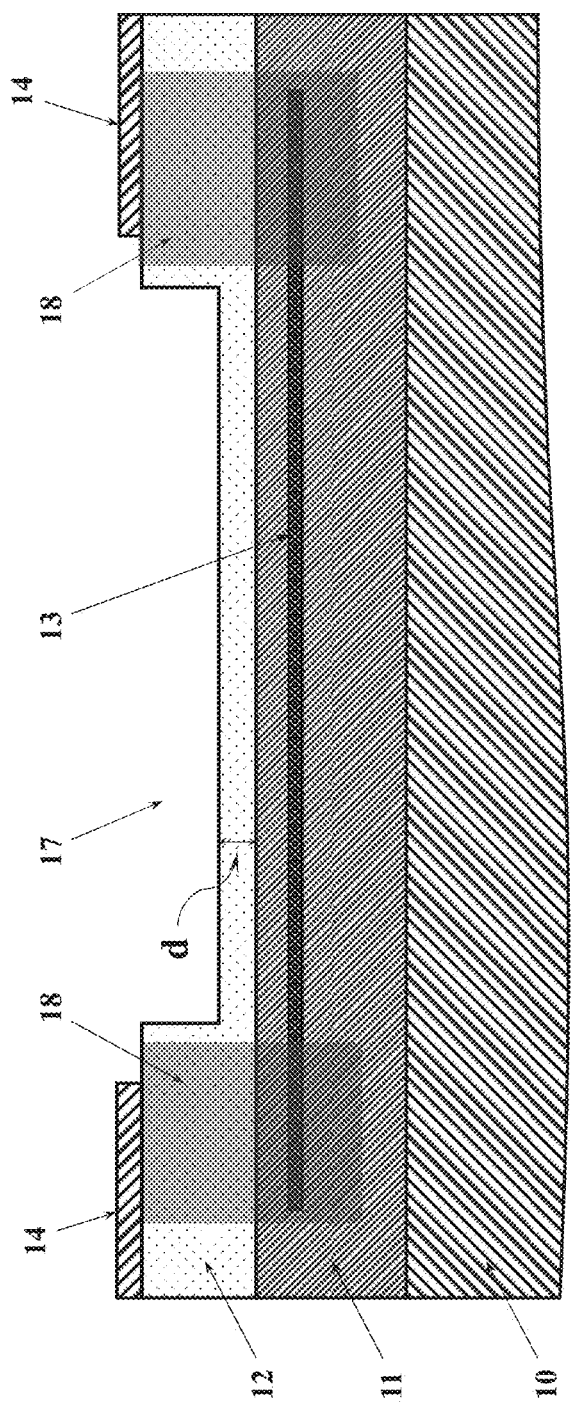
FIG. 2d schematically shows a cross-sectional view of the PC-HEMT of an embodiment with highly-doped source and drain areas.

Reference is now made to FIG. 2d that schematically shows a cross-sectional view of the PC-HEMT of an embodiment of the present application with highly-doped source and drain areas (18). In that case, the strong doping of the source and drain areas may result in a band-edge mismatch. However, if the semiconductor is doped strongly enough, it will form a certain potential barrier, low enough for conducting electrons to have a high probability of tunnelling through this barrier, and therefore conducting an electric current through the 2DEG channel.

An electrical connection to the 2DEG channel shown in FIG. 2d is realised with highly doped semiconductor areas (18) overlapping the 2DEG channel and having a very low electrical resistance. Dopant ions such as boron ($B^+$), phosphorus ($P^+$) or arsenic ($As^+$) are generally created from a gas source, so that the purity of the source can be very high. When implanted in a semiconductor, each dopant atom creates a charge carrier in the semiconductor material after annealing. Holes are created for a p-type dopant, and electrons are created for an n-type dopant, modifying conductivity of the semiconductor in its vicinity. $As^+$ can be used for n-type doping, while $B^+$ and $P^+$ ions can be used for p-type doping. For example, in case of the AlGaN/GaN structure, the source and drain areas of the silicon structure are heavily doped with either $B^+$ or $P^+$ to create an electrical connection to the 2DEG channel. The silicon layers have a very low electrical junction resistance between each other in that case, and in order to induce an electrical current in the 2DEG channel, the metallizations are placed on top of the source and drain areas and connected to a circuit.

The third option would be the use of the photo effect that may also induce an electric current in the 2DEG channel. In order to couple the light excitation with the electronic effects in the conductive 2DEG channel, a photo effect in a silicon layer should be created. Regarding the direct photo effect, it is well known that light can only be absorbed when the energy of the absorbed photon (E=hv) is large enough for an electron to be excited into the valence band. In that case, E is the photon energy, h is Planck's constant and v is the frequency of the photon. The frequency is coupled to the wavelength λ of light by the constant speed of light c=λv. Typically the bandgap of silicon at room temperature is 1.12.eV, which means that silicon becomes transparent for wavelength larger than 1240 nm, which is the near infrared range.

For smaller wavelength (i.e. larger energy of the photons), electron/hole pairs are generated leading to a photocurrent. In the fully-depleted, intrinsically doped silicon structures, this results in a higher charge carrier density and consequently, higher sensitivity. For these structures, light is adsorbed in the whole visible range making such devices ideal photodetectors. The mechanism that allows the silicon semiconductor to become photosensitive to irradiation with light has already been described in literature. In the direct photo effect, it can be tuned by the size, crystalline direction and surface termination. These effects actually originate from two-dimensional quantum confinement of electrons in the nano-sized 2DEG structure.

Although irradiation of the silicon structure with light of larger wavelengths with photon energies below the bandgap does not have enough energy to excite carriers from the valence to the conduction band in bulk silicon, the electron/hole pairs can also be generated between the valence band and surface states, and the donor-like surface trap states can still be formed (see the definition and explanation of the surface trap states below). The electrons actually deplete these holes trapped at the surface and hence, modulate the gate field. The photogenerated holes are confined to the centre of the silicon structure by the gate field, where they increase the conduction of the 2DEG channel, because of the band bending. The holes increase the channel conductivity for a certain lifetime until they are trapped (recaptured) at the surface. The gain of the transistor can be extremely huge if this re-trapping lifetime is much longer than the holes transit time.

If the source and drain contacts are non-ohmic (capacitively-coupled), in order to electrically contact the 2DEG channel underneath, which is about 7-20 nm bellow metallizations (14), the AC frequency regime is used. The capacitive coupling of the non-ohmic metal contacts with the 2DEG channel is normally induced at the frequency higher than 30 kHz. In the case of the non-ohmic contacts, the DC readout cannot be performed. Instead, the AC readout or impedance measurements of the electric current flowing through the 2DEG channel are carried out.

In some embodiments, the significant features of the PC-HEMT structure are that:
(i) the non-ohmic source and drain contacts for the capacitive coupling with the conductive 2DEG channel are used,
(ii) the thickness of the top barrier layer in the open gate area is 5-9 nm, preferably 6-7 nm, more preferably 6.3 nm, which corresponds to the pseudo-conducting current range between normally-on and normally-off operation mode of the transistor, and
(iii) the surface of the top barrier layer has a roughness of 0.2 nm or less, preferably 0.1 nm or less, more preferably 0.05 nm.

Figure 2E:
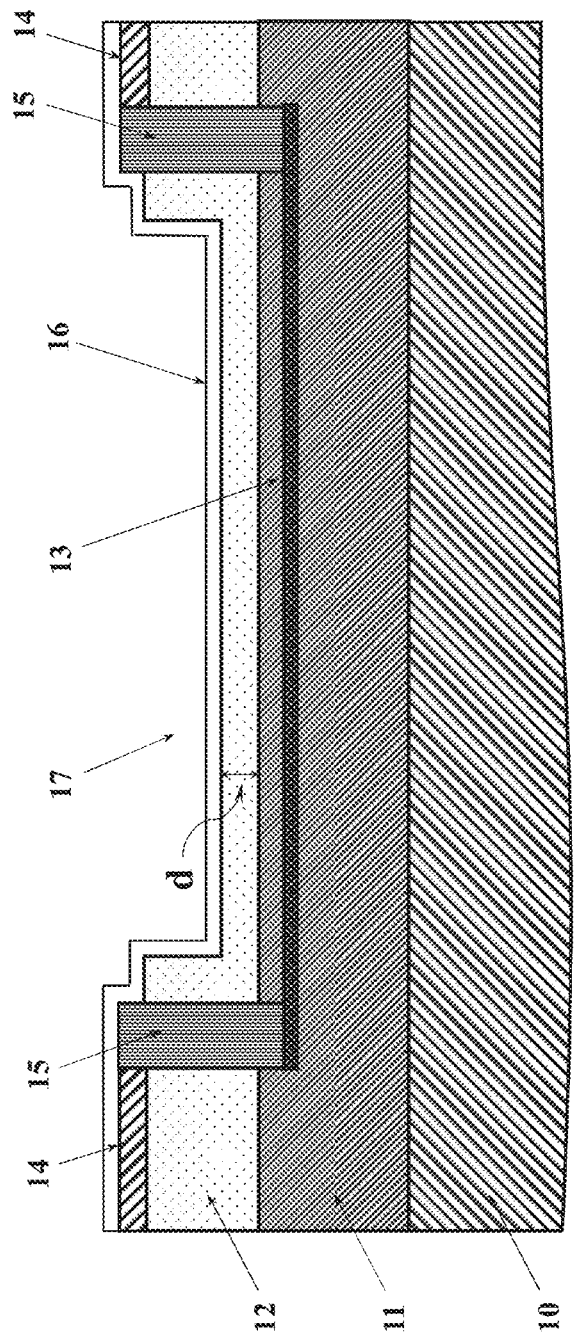
FIG. 2e schematically shows a cross-sectional view of the PC-HEMT of an embodiment with a dielectric layer.
Figure 2F:
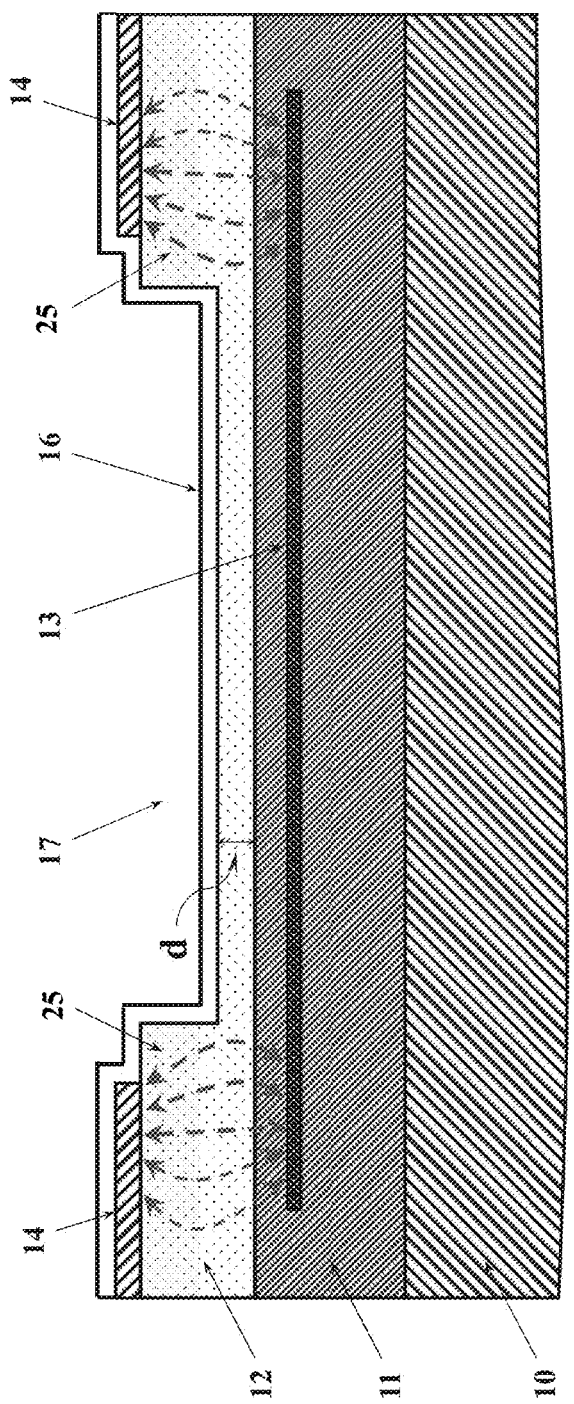
FIG. 2f schematically shows a cross-sectional view of the PC-HEMT of an embodiment having non-ohmic (capacitively-coupled) contacts and a dielectric layer.

The same transistors of the embodiments depicted in FIGS. 2a and 2c, but further comprising a dielectric layer (16), which is deposited on top of the barrier layer (12), are schematically shown in FIGS. 2e and 2f, respectively. In one embodiment, the optional dielectric layer (16), which is used for device passivation, is made, for example, of SiO—SiN—SiO ("ONO") stack of 100-100-100 nm thickness or SiN—SiO—SiN ("NON") stack having the same thicknesses. This dielectric layer (16) is deposited on top of the barrier layer by a method of plasma-enhanced chemical vapour deposition (PECVD), which is a stress-free deposition technique.

In a specific embodiment, the III-V semiconductor materials may be selected from GaN/AlGaN, GaN/AlN, GaN/InN, GaN/InAlN, InN/InAlN, GaN/InAlGaN, GaAs/AlGaAs and $LaAlO_3/SrTiO_3$.

The electrical metallizations (14) connect the PC-HEMT to an electric circuit and allow electric current to flow between the source and drain contacts. The electrical metallizations (14) are made of metal stacks, such as Cr/Au, Ti/Au, Ti/W, Cr/Al and Ti/Al. The Cr or Ti layers of the metal stack is, for example, of 5-10 nm thickness, while the second metal layer, such as Au, W and Al, is of 100-400 nm thickness. The actual metallizations (14) are chosen according to the established technology and assembly line at a particular clean room fabrication facility. The source and drain ohmic contacts are usually made of metal stacks, such as Ti/Al/Mo/Au, Ti/Al/Ni/Au, Ti/Au and Ti/W having 15-50 nm thickness. The non-ohmic contacts on the other hand are capacitively coupled to the conducting 2DEG channel (13) via displacement currents (25).

In yet further embodiment, substrate layer (10) comprises a suitable material for forming the barrier layer and is composed, for example, of sapphire, silicon, silicon carbide, gallium nitride or aluminium nitride. The hetero-junction structure (11, 12) is deposited on the substrate layer (10), for example, by a method of metalorganic chemical vapour deposition (MOCVD), and forms a two-dimensional electron gas (2DEG) channel (13) in the close proximity to the interface between the buffer layer (11) and the top barrier layer (12). The top barrier layer (12) then may be either recessed or grown as a thin layer between the source and drain contacts, thereby forming an open gate area.

The 2DEG channel (13) formed near the interface between the buffer layer (11) and the barrier layer (12) serves as a main sensitive element of the transistor reacting to a surface charge and potential. The 2DEG channel (13) is configured to interact with very small variations in surface or proximal charge or changes of electrical field on the barrier layer/liquid-air or barrier layer/metal/liquid-air interfaces interacting with the donor-like surface trap states of the barrier layer. This will be defined and discussed below in detail.

"Open gate area" of the PC-HEMT is defined as an area between the source and drain contacts of the transistor which is directly exposed to a conductive medium, such as liquid or gas capable of conducting current. An example of the conductive liquid is an electrolyte saline solution. In this case, instead of the fixed gate voltage, which is normally applied to a gate electrode, a reference potential is applied to the electrolyte-semiconductor system, via an optional reference electrode that is dipped into the electrolyte. As a result, in the absence of the physical gate, the electrolyte itself becomes an open gate of the transistor. This will be explained in more detail below.

The specific thickness of the top barrier layer (12) in the open gate area is achieved by either dry etching the semiconductor material of the barrier layer (12), i.e. recessing the layer in the open gate area with the etching rate of 1 nm per 1-2 min in a controllable process, or coating the buffer layer (11) in the open gate area with an ultrathin layer of the III-V semiconductor material. In order to increase the charge sensitivity of the transistor, the surface of the recessed ultrathin barrier layer is post-treated with plasma (chloride) epi-etch process. Consequently, the natively passivated surface is activated by the plasma etch to create an uncompensated (ionised) surface energy bonds or states, which are neutralized after MOCVD growing.

Figure 3:
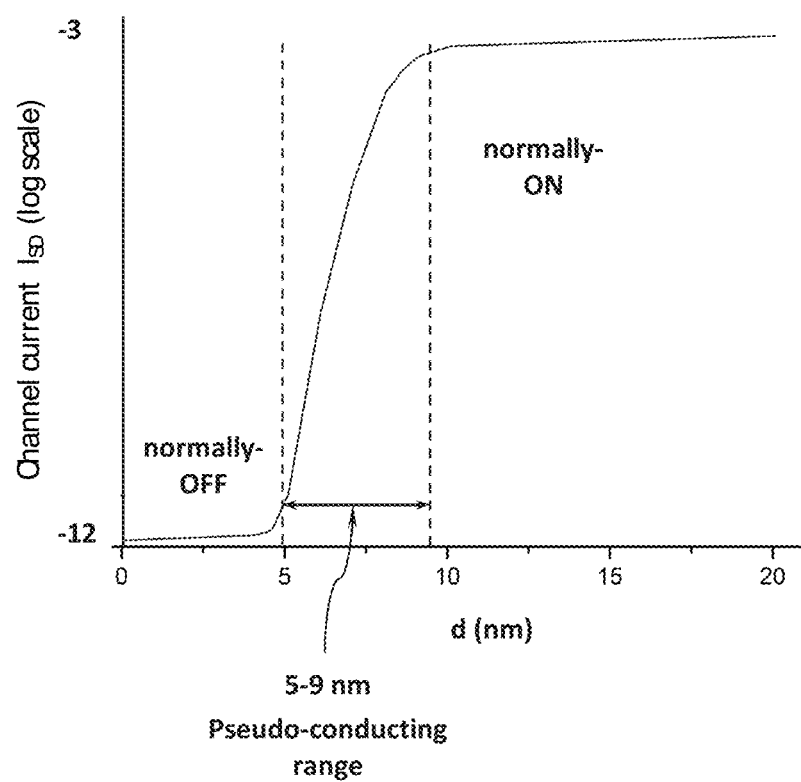
FIG. 3 schematically shows the dependence of the source-drain current (a charge carrier density) induced inside the 2DEG channel of a GaN/AlGaN HEMT on the thickness of the AlGaN barrier layer recessed in the open gate area.

FIG. 3 shows the dependence of the source-drain current (a charge carrier density) on the barrier layer thickness recessed in the open gate area. As seen from the plot, the HEMTs that have a thickness of the barrier layer in the open gate area larger than about 9 nm are normally-on devices. In such devices, due to the inherent polarisation effects present in the III-V materials, a thin sheet of charges is induced at the top and bottom of the interfaces of the barrier layer. As a result, a high electric field is induced in the barrier layer, and surface donor states at the top interface start donating electrons to form the 2DEG channel at the proximity of the hetero-junction interface without the application of a gate bias. These HEMTs are therefore normally-on devices. On the other hand, the HEMTs that have a thickness of the barrier layer in the open gate area lower than about 5 nm act as normally-off devices.

The top barrier layer recessed or grown in the open gate area to 5-9 nm is optimised for significantly enhancing sensitivity of the PC-HEMT sensor. This specific thickness of the top barrier layer in the open gate area corresponds to the "pseudo-conducting" current range between normally-on and normally-off operation modes of the transistor and requires further explanation.

"Pseudo-conducting" current range of the HEMT is defined as an operation range of the HEMT between its normally-on and normally-off operation modes. "Trap states" are states in the band-gap of a semiconductor which trap a carrier until it recombines. "Surface states" are states caused by surface reconstruction of the local crystal due to surface tension caused by some crystal defects, dislocations, or the presence of impurities. Such surface reconstruction often creates "surface trap states" corresponding to a surface recombination velocity. Classification of the surface trap states depends on the relative position of their energy level inside the band gap. The surface trap states with energy above the Fermi level are acceptor-like, attaining negative charge when occupied. However, the surface trap states with energy below the Fermi level are donor-like, positively charged when empty and neutral when occupied. These donor-like surface trap states are considered to be the source of electrons in the formation of the 2DEG channel. They may possess a wide distribution of ionization energies within the band gap and are caused by redox reactions, dangling bonds and vacancies in the surface layer. A balance always exists between the 2DEG channel density and the number of ionised surface donors which is governed by charge neutrality and continuity of the electric field at the interfaces.

Thus, the donor-like surface traps formed at the surface of the barrier layer of the HEMT are one of the most important sources of the 2DEG in the channel. However, this only applies for a specific barrier layer thickness. In a relatively thin top barrier layer, the surface trap state is below the Fermi level. However, as the top barrier layer thickness increases, the energy of the surface trap state approaches the Fermi energy until it coincides with it. The thickness of the top barrier layer corresponding to such situation is defined as "critical". At this point, electrons filling the surface trap state become pulled to the channel by the strong polarisation-induced electric field found in the barrier to form the 2DEG instantly.

If the surface trap states are completely depleted, further increase in the barrier layer thickness will not increase the 2DEG density. Actually, if the 2DEG channel layer fails to stretch the barrier layer, the later will simply relax. Upon relaxation of the barrier layer, crystal defects are created at the interface between the buffer layer and the barrier layer, and the piezoelectric polarisation instantly disappears causing deterioration in the 2DEG density.

Figure 4:
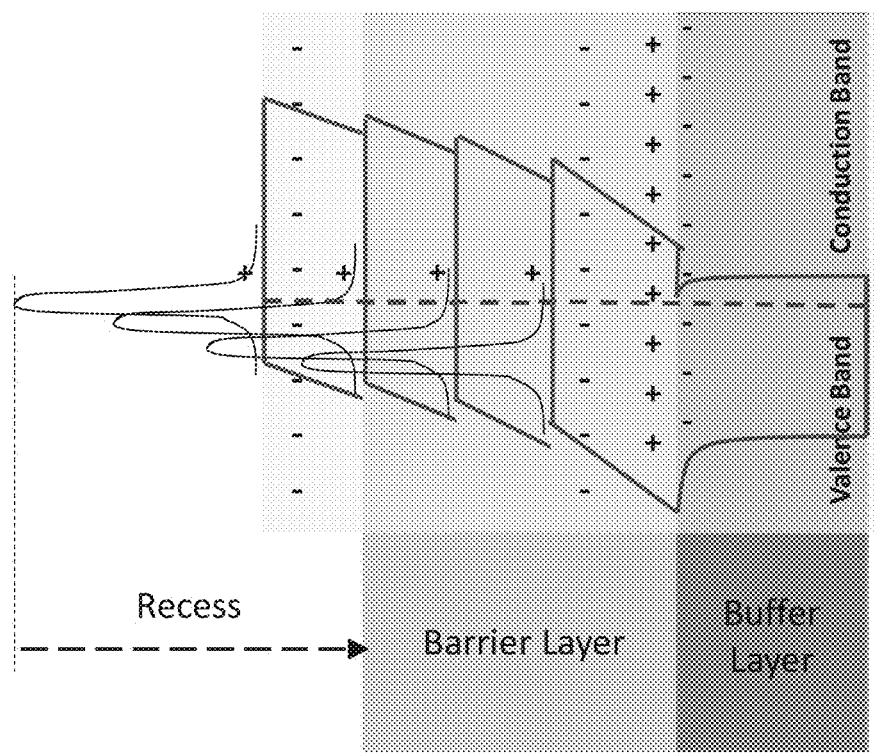
FIG. 4 illustrates a theory behind the 2DEG formation (charge neutrality combined with the lowest energy level) at the conduction band discontinuity.

In order to illustrate the above phenomenon of pseudo-conducting current, reference is now made to the following figures. As mentioned above, FIG. 3 shows the dependence of the source-drain current (a charge carrier density) on the recessed AlGaN barrier layer thickness. An energy equilibrium between the donor surface trap states and the AlGaN tunnel barrier leads to the 2DEG formation (charge neutrality combined with the lowest energy level) at the conduction band discontinuity. As explained above, decrease in the thickness of the top barrier layer results in increase of the energy barrier. As a result, the ionisable donor-like surface trap states, which are responsible for electron tunnelling from the surface to 2DEG, drift bellow the Fermi level, thereby minimizing the electron supply to the 2DEG channel. This theoretical situation is illustrated in FIG. 4. Therefore, the recess of the top AlGaN layer from 9 nm to 5 nm leads to extremely huge drop in the 2DEG conductivity for six orders of magnitude.

In view of the above, it is clear that the mechanism of the 2DEG depletion based on recessing the top barrier layer is strongly dependent on the donor-like surface trap states (or total surface charge). As the thickness of the barrier layer decreases, less additional external charge is needed to apply to the barrier layer surface in order to deplete the 2DEG channel. There is a critical (smallest) barrier thickness, when the 2DEG channel is mostly depleted but still highly conductive due to a combination of the energy barrier and the donor surface trap states energy. At this critical thickness, even the smallest energy shift at the surface via any external influence, such as surface reaction, charging etc., leads immediately to very strong 2DEG depletion. As a result, the surface of the top barrier layer at this critical thickness is extremely sensitive to any smallest change in the electrical field of the surroundings.

Thus, the recess of the gate area of the barrier layer from 9 nm down to 5 nm significantly reduces the 2DEG density, brings the transistor to the "near threshold" operation and results in highly increased surface charge sensitivity. The specific 5-9 nm thickness of the top barrier layer responsible for the pseudo-conducting behaviour of the transistor gives the sensor an incredible sensitivity. So, when it comes into a contact with an ionic fluid or body skin, it opens up the gate to be able to do the ultrasensitive sensing.

The top layer is recessed to this specific thickness after subjecting to short plasma activation by an ultra-low damage reactive-ion etching technique using inductively-coupled plasma (ICP) with a narrow plasma-ion energy distribution. Such short plasma treatment allows much lower roughness of the surface, which is a function of the semiconductor vertical damage depth during the plasma etching process. Such low surface roughness (about 0.2 nm and less) can be achieved only via this ICP-RIE ultra low damage etching process with a narrow plasma-ion energy distribution, and this inherently results in a very low vertical damage depth to the top layer, which allows the minimal surface scattering and minimal surface states-2DEG channel interaction with the maximum signal-to-noise ratio of the sensor. Thus, the depth effect of the vertical sub-nanometre damage to the top recessed layer, due to an ultra-low damage ICP-RIE etching process with a very narrow plasma-ion energy distribution, is the only way to optimally achieve the required sub-nanometre roughness of the semiconductor surface. This inherently results in an adjustable pseudo-conductive working point with the highest charge sensitivity ever possible. This depth effect is always inherent to the sub-nanometre roughness of the semiconductor surface, which was measured using AFM (atomic force microscope).

Thus, in addition to the recessed top layer thickness, roughness of the layer surface is another very important parameter that has not been previously disclosed. It has been surprisingly found that the roughness of the top layer surface (in the open gate sensitive area) bellow 0.2 nm prevents scattering of the donor-like surface trap states. Thus, the combination of these two features: 5-9 nm thickness of the top layer in the open gate area and strongly reduced roughness of its surface make the PC-HEMT an incredibly strong functional amplifier.

In a certain aspect, the method for manufacturing of the PC-HEMTs of the present invention comprises the following steps:

Step 1: Plasma-enhanced atomic layer deposition (ALD) of alumina ($Al_2O_3$) on a pre-aligned masked Si—GaN/AlGaN wafer with nitrogen-plasma de-trapping for the thickness of the $Al_2O_3$ layer being 3-10 nm. The $Al_2O_3$ layer thickness was measured with an X-ray reflectometer.

Step 2: Plasma-enhanced atomic layer deposition (ALD) patterning of the wafer coated with the thin $Al_2O_3$ layer in Step 1, with hydrogen fluoride (HF) or using the aforementioned reactive-ion etching (RIE) technique.

Step 3: Optionally creating the source and drain ohmic contacts (in case ohmic contacts are required) on the coated wafer obtained in Step 2 from metal stacks, for example Ti/Al/Mo/Au, Ti/Al/Ni/Au, Ti/Au and Ti/W, having 15-50 nm thickness, using spin-coating technique or e-beam physical vapour deposition (VPD) of the stack metals. The deposition rates using the e-VPD technique were determined for the ohmic-stack metals using the Dektak Profilometer with dummy lift-off samples.

Step 4: Two-dimensional electron gas (2DEG) channel-patterning of the wafer obtained in Step 3 with argon- or nitrogen-ion implantation.

Step 5: Plasma-enhanced chemical vapour deposition (CVD) of the ONO stack over the wafer obtained in Step 4. This is the stress-free technique to deposit the layer of the SiO—SiN—SiO stack having an exemplary thickness of about 200-300 nm and structured by the ICP-RIE dry etching, which is the CF4-based etching method. In this step, the pseudo-conducting channel areas and ohmic electrical contact pads of the transistor become available.

Step 6: Optional lift-off deposition of an Au or Ti/W-CMOS-gate electrode (in case a gate electrode is to be deposited on the top layer of the heterojunction structure for an integrated MMIC-HEMT-based amplifier manufacturing).

Step 7: Optional plasma-enhanced ALD pattering with RIE or HF above sensing area (in case the plasma-enhanced ALD layer deposited in Step 1 is removed separately to ONO stack).

Step 8: Atomic layer etching (ALE) of the wafer obtained in Steps 5-7. This sophisticated technique carried out in the clean manufacturing cluster of the applicant is the only technique allowing the removal of individual atomic layers (the top atomic layers of the wafer). ALE is a way better-controlled technique than RIE, though it has not been commercially used until now because very sophisticated gas handling is required, and removal rates of one atomic layer per second are the real state of the art. This step is the step of creating the pseudo-conducting working point of the transistor, because ALE allows achieving the specific thickness of 5-9 nm thickness of the top layer in the open gate area with the extremely low surface roughness of the top layer below 0.2 nm.

Step 9: Optional plasma-enhanced CVD or ALD of the dielectric layer used for device passivation and in some gas sensors.

Step 10: Optional deep reactive-ion etching (DRIE or Bosch process) of the Si-substrate under sensing areas (in case the substrate is on the free-standing membranes—used, for example, in RF-HEMTs, FBAR and SAW sensors).

Figure 5A:
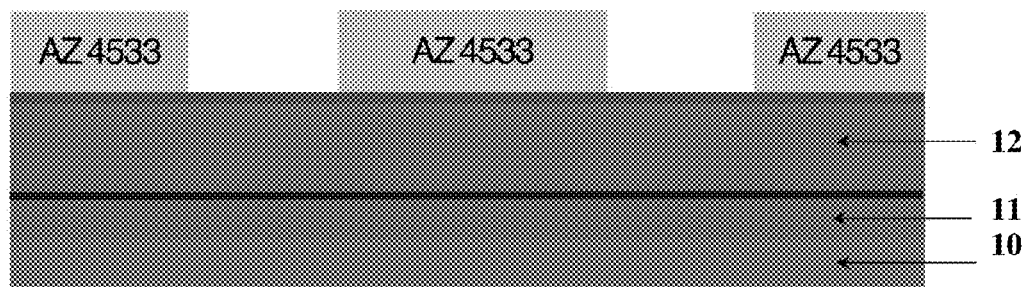
FIG. 5a schematically shows the 2DEG area created in the step of the 2DEG-pattering via ion implantation during the manufacturing process. AZ 4533 is a positive thick resist.
Figure 5B:
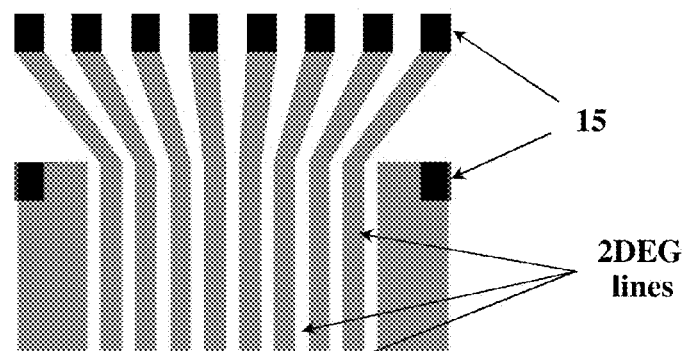
FIG. 5b shows the lithographic mask of the sensor layout of the present invention.
Figure 5C:
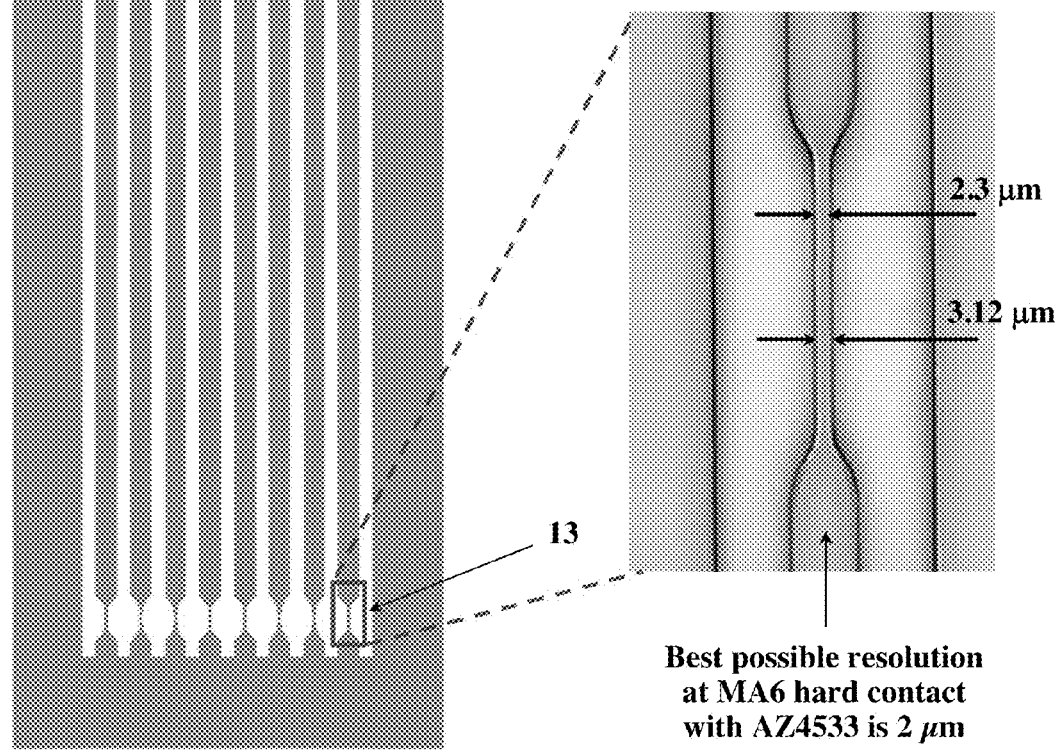
FIG. 5c shows the lithographic image of the 2DEG channel formed with AZ 4533 thick resist lithography over the mask shown in FIG. 5b.

Reference is now made to FIGS. 5a-5c showing the sensor, which is obtained in Step 4 of the 2DEG-channel pattering. The lithography of the sensor was performed with AZ 4533, which is a positive thick resist having optimised adhesion for common wet etching. The lithographic resist film thickness obtained at 7000-rpm spin speed and at 100° C. for 1 min was 3 μm. Thus, as seen in the lithographic image of FIG. 5c, the formed 2DEG channel (13) is approximately 2-3 μm wide. The overall exposure time was 9 sec, followed by 5-min development in MIF726 developer.

Figures 5D, 5E:
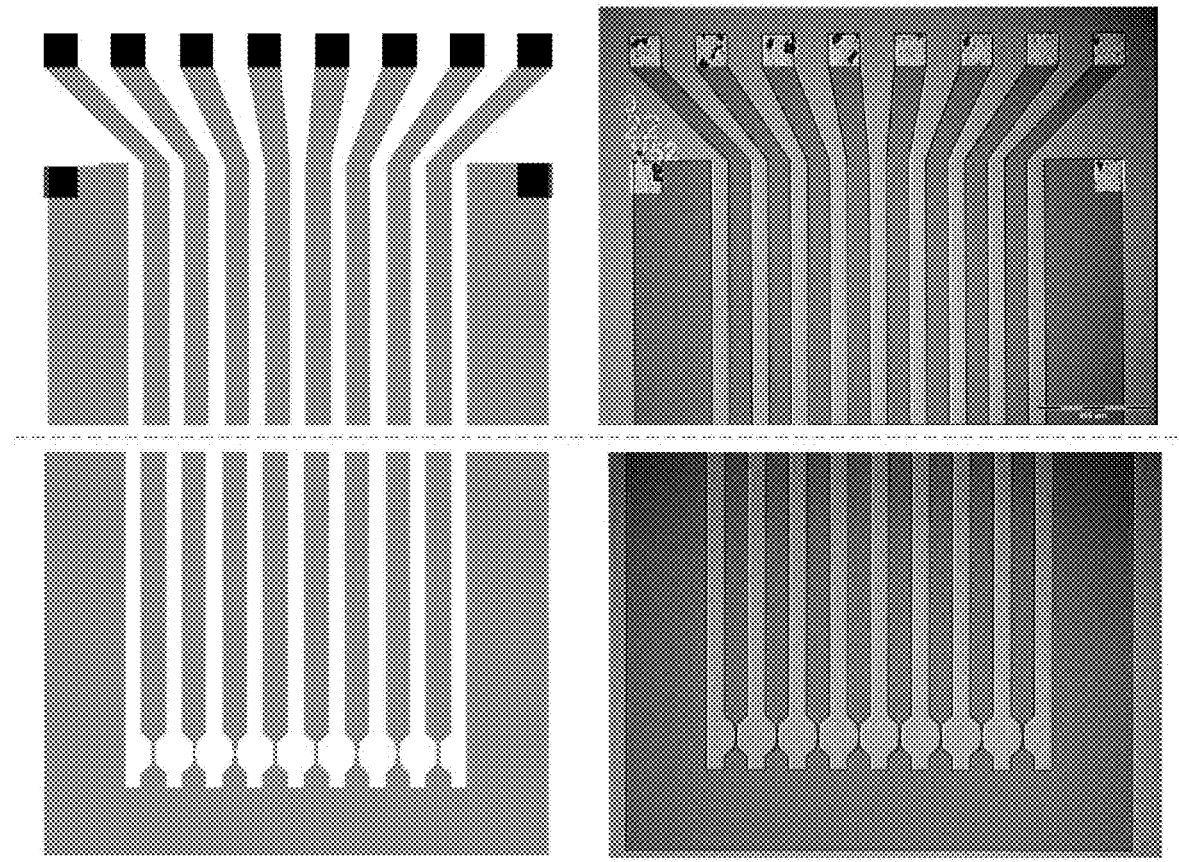
FIGS. 5d-5e show the mask and the corresponding lithographic image, respectively, of the sensor layout of the present invention.
Figure 5F:
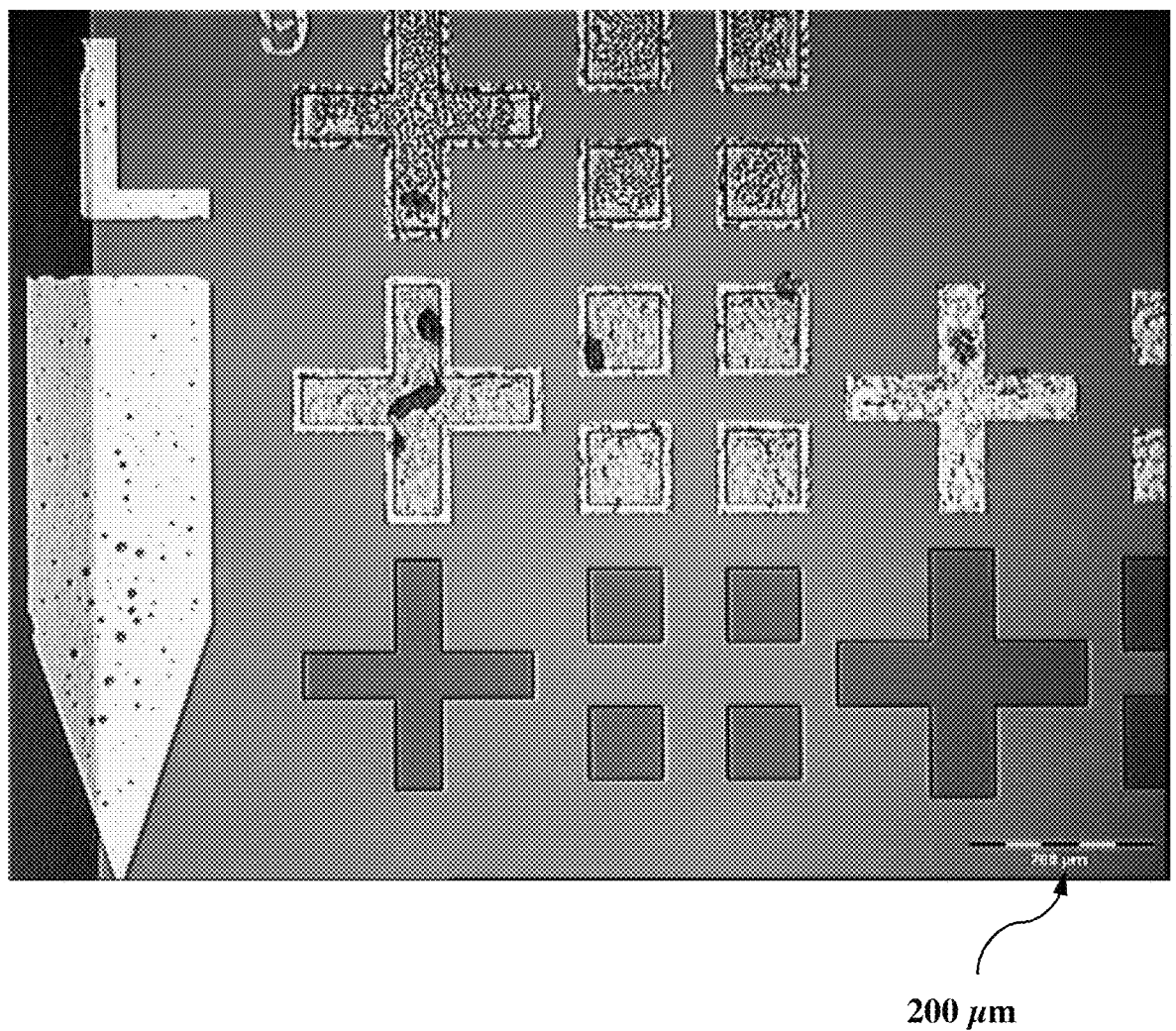
FIG. 5f shows the ±2-µm alignment precision on 25×25 $mm^2$ samples in the lithography of the sensor layout of the present invention.
Figure 5H:
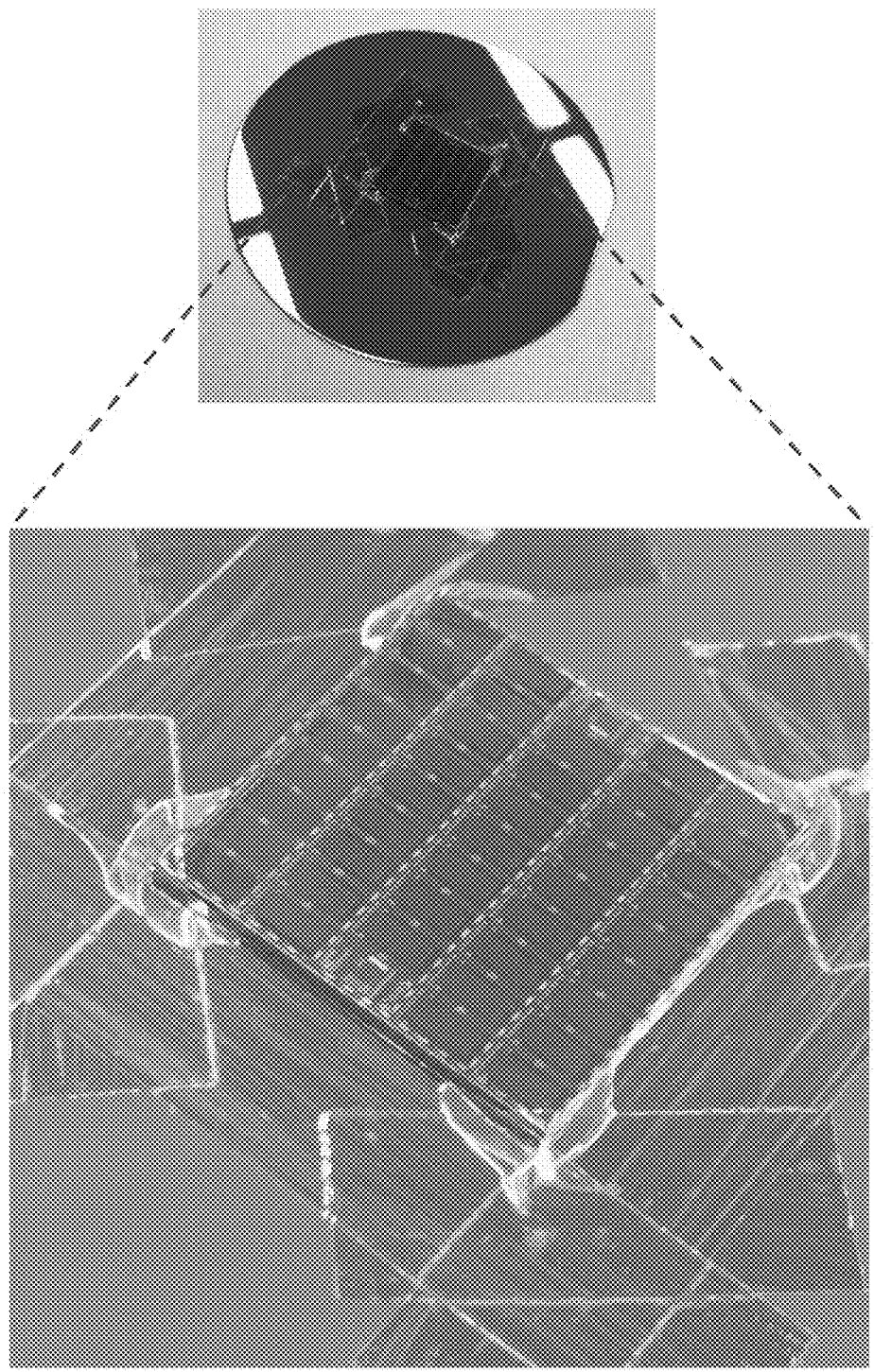
FIG. 5h shows the fixed sample on the Si—GaN/AlGaN wafer prepared for ion implantation and containing around 30-32 sensors with 4-8 channels on each sample.

FIG. 5d-5e show the mask and corresponding lithographic image, respectively, of the sensor layout of the present invention. FIG. 5f demonstrates the high alignment precision of ±2-μm on 25×25 mm$^2$ samples in the lithography of the sensor layout of the present invention. FIG. 5g shows the lithographic images of the multichannel samples. FIG. 5h shows the fixed sensor chip sample on the Si—GaN/AlGaN wafer, which contains approximately 30-32 sensors with 4-8 channels on each sample and prepared for ion implantation. FIG. 5i shows the obtained lithographic image of the present sensor layout with the AZ4533 resist after development, prepared for ion implantation. FIG. 5j shows the 2DEG channels (dark) patterned by ion-implantation after the resist removal. The argon-ion implantation was conducted with 20 keV and 30 keV energies and with an exemplary dose of 2.5 e$^{13}$/cm$^2$ and a 7° tilt angle. AZ4533 was removed with oxygen plasma at 220 W for 10 min. FIG. 5k shows the visible non-implanted area containing the conductive 2DEG channel.

The atomic layer etching (ALE) performed in Step 8 of the manufacturing process is the most important stage in the process. As mentioned above, it allows the controlled recess of a top layer, removing a single atomic layer-by-layer, where the etch thickness is in the order of magnitude of a single atomic monolayer. As explained above, such ultra-low damage to the top layer of the heterogeneous structure, when the actual surface roughness is controlled by a single atomic monolayer, allows to achieve the sub-nanometre roughness (about 0.2 nm and less) of the top layer when its thickness is only few nanometres (5-9 nm).

The ALE process sequence consists of repeated cycling of process conditions. The total amount of material removed is determined by the number of repeated cycles. Each cycle is typically comprised of four steps: adsorption, first purge, desorption and second purge. During the adsorption step of the cycle, reactive species are generated in the reactor (for example, upon plasma excitation), adsorbed by, and react with material on the wafer. Due to the self-limiting process, and with the proper choice of reactants and process conditions, reaction takes place with only a thin layer of material, and the reaction by-products are formed. This step is followed by purging of the reactor to remove all traces of the reactant. Then the by-product desorption takes place due to bombardment of the wafer surface by noble gas ions with a tightly controlled energy. Again, by-products are purged from the reactor, and the wafer is ready for the last two (optional) steps of the manufacturing process.

In a further aspect, the hetero-junction structure may be a three-layer structure consisting of two buffer layers and one barrier layer squeezed between said buffer layers like in a sandwich, wherein the top layer is a buffer layer. This may lead to formation of the two-dimensional hole gas (2DHG) in the top buffer layer above the barrier layer which results in reversing polarity of the transistor compared to the two-layer structure discussed above.

In general, polarity of III-V nitride semiconductor materials strongly affects the performance of the transistors based on these semiconductors. The quality of the wurtzite GaN materials can be varied by their polarity, because both the incorporation of impurities and the formation of defects are related to the growth mechanism, which in turn depends on surface polarity. The occurrence of the 2DEG/2DHG and the optical properties of the hetero-junction structures of nitride-based materials are influenced by the internal field effects caused by spontaneous and piezo-electric polarizations. Devices in all of the III-V nitride materials are fabricated on polar {0001} surfaces. Consequently, their characteristics depend on whether the GaN layers exhibit Ga-face positive polarity or N-face negative polarity. In other words, as a result of the wurtzite GaN materials polarity, any GaN layer has two surfaces with different polarities, a Ga-polar surface and an N-polar surface. A Ga-polar surface is defined herein as a surface terminating on a layer of Ga atoms, each of which has one unoccupied bond normal to the surface. Each surface Ga atom is bonded to three N atoms in the direction away from the surface. In contrast, an N-polar surface is defined as a surface terminating on a layer of N atoms, each of which has one unoccupied bond normal to the surface. Each surface N atom is also bonded to three Ga atoms in the direction away from the surface. Thus, the N-face polarity structures have the reverse polarity to the Ga-face polarity structures.

As described above for the two-layer heterojunction structure, the barrier layer is always placed on top of the buffer layer. The layer which is therefore recessed is the barrier layer, specifically the AlGaN layer. As a result, since the 2DEG is used as the conducting channel and this conducting channel is located slightly below the barrier layer (in a thicker region of the GaN buffer layer), the hetero-junction structure is grown along the {0001}-direction or, in other words, with the Ga-face polarity. However, as explained above, the physical mechanism that leads to the formation of the 2DEG is a polarisation discontinuity at the AlGaN/GaN interface, reflected by the formation of the polarisation-induced fixed interface charges that attract free carriers to form a two-dimensional carrier gas. It is a positive polarisation charge at the AlGaN/GaN interface that attracts electrons to form 2DEG in the GaN layer slightly below this interface.

As noted above, polarity of the interface charges depends on the crystal lattice orientation of the hetero-junction structure, i.e. Ga-face versus N-face polarity, and the position of the respective AlGaN/GaN interface in the hetero-junction structure (above or below the interface). Therefore, different types of the accumulated carriers can be present in the hetero-junction structure of the embodiments.

In case of the three-layer hetero-junction structure, there are four possible configurations:

Ga-Face Polarity
1) The Ga-face polarity is characterised by the 2DEG formation in the GaN layer below the AlGaN barrier layer. This is actually the same two-layer configuration as described above, but with addition of the top GaN layer. In this configuration, the AlGaN barrier layer and two GaN buffer layers must be nominally undoped or n-type doped.
2) In another Ga-face configuration shown in FIG. 6a, in order to form the conducting channel comprising a two-dimensional hole gas (2DHG) in the top GaN layer above the AlGaN barrier layer in the configuration, the AlGaN barrier layer should be p-type doped (for example, with Mg or Be as an acceptor) and the GaN buffer layer should be also p-type doped with Mg, Be or intrinsic.

N-Face Polarity
3) The N-face polarity is characterised by the 2DEG formation in the top GaN layer above the AlGaN barrier layer, as shown in FIG. 6b. In this case, the AlGaN barrier layer and two GaN buffer layers must be nominally undoped or n-type doped.
4) The last configuration assumes that the 2DHG conducting channel is formed in the buffer GaN layer below the AlGaN barrier layer. The top GaN layer may be present (three-layer structure) or not (two-layer structure) in this case. The AlGaN barrier layer must be p-type doped (for example, with Mg or Be as an acceptor) and the bottom GaN layer should be also p-type doped with Mg, Be or intrinsic.

Thus, there are four hetero-junction three-layer structures implemented in the transistor of the embodiments, based on the above configurations:

A. Ga-Face GaN/AlGaN/GaN heterostructure with the 2DEG formed in the GaN buffer layer below the AlGaN barrier layer. In this case, the top GaN layer may be omitted to obtain the two-layer structure. For the three-layer structure, the top GaN layer must be recessed to 1-9 nm thickness in the open gate area or grown with this low thickness, with the roughness below 0.2 nm, and the thickness of the AlGaN barrier can be adjusted properly during growth B. Ga-Face GaN/AlGaN/GaN heterostructure with the 2DHG conducting channel formed in the top GaN layer above the AlGaN barrier layer. The top GaN layer must be recessed to 5-9 nm thickness in the open gate area with the roughness below 0.2 nm, and the thickness of the AlGaN barrier layer can be adjusted properly. P-type doping concentrations of the GaN layer and AlGaN barrier have to be adjusted; the 2DHG has to be contacted (in the ideal case by ohmic contacts).

C. N-Face GaN/AlGaN/GaN heterostructure with the 2DEG in the top GaN layer above the AlGaN barrier layer. The top GaN layer must be recessed to 5-9 nm thickness in the open gate area with the roughness below 0.2 nm. Thickness of the AlGaN barrier can be adjusted during growth. N-type doping levels of the GaN buffer layer and the AlGaN barrier layer must be adjusted; the 2DEG has to be contacted (in the ideal case by ohmic contacts).

D. N-Face GaN/AlGaN/GaN heterostructure with the 2DHG in the GaN buffer layer below the AlGaN barrier layer. In this case, the top GaN layer may be omitted to obtain the two-layer structure. In both, the two-layer and three-layer configurations, the top GaN layer must be recessed to 1-9 nm thickness in the open gate area with the roughness below 0.2 nm, and the thickness of the AlGaN barrier can be adjusted properly.

Figure 7:
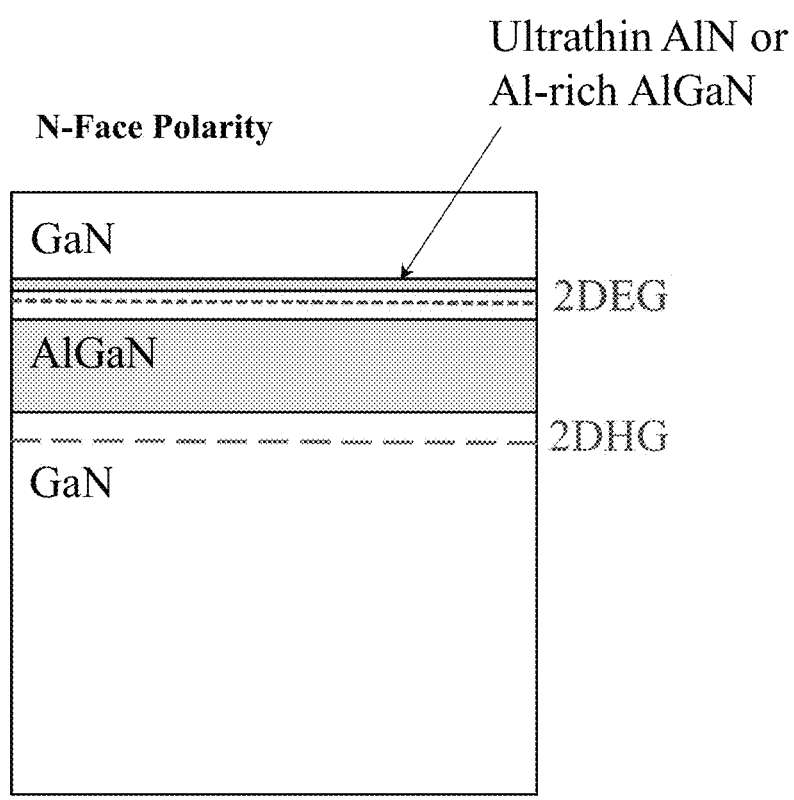
FIG. 7 schematically shows the formation of the 2DEG conducting channel in the N-face three-layer GaN/AlGaN/GaN PC-HEMT structure with an ultrathin Al(GaN)N layer for improved confinement.

In all the above structures, the deposition of a dielectric layer on top might be beneficial or even necessary to obtain a better confinement (as in case of the N-face structures). As shown in FIG. 7, for the above "C" structure, it may be even more beneficial to include an ultrathin (about 1 nm) AlN or AlGaN barrier layer with high Al-content on top of the 2DEG channel to improve the confinement.

The preferable structures of the embodiments are structures "B" and "C". In the structure "B", the 2DHG conducting channel formed in the top GaN layer, which has a higher chemical stability (particularly towards surface oxidation) than the AlGaN layer. Concerning the structure "C", the 2DEG conducting channel might be closer to the surface. Therefore, the electron mobility might be lower than in the 2DEG structure with the Ga-face polarity. In general, the polarity of the heterostructure can be adjusted by the choice of the substrate (e.g. C-face SiC) or by the growth conditions.

Figure 8:
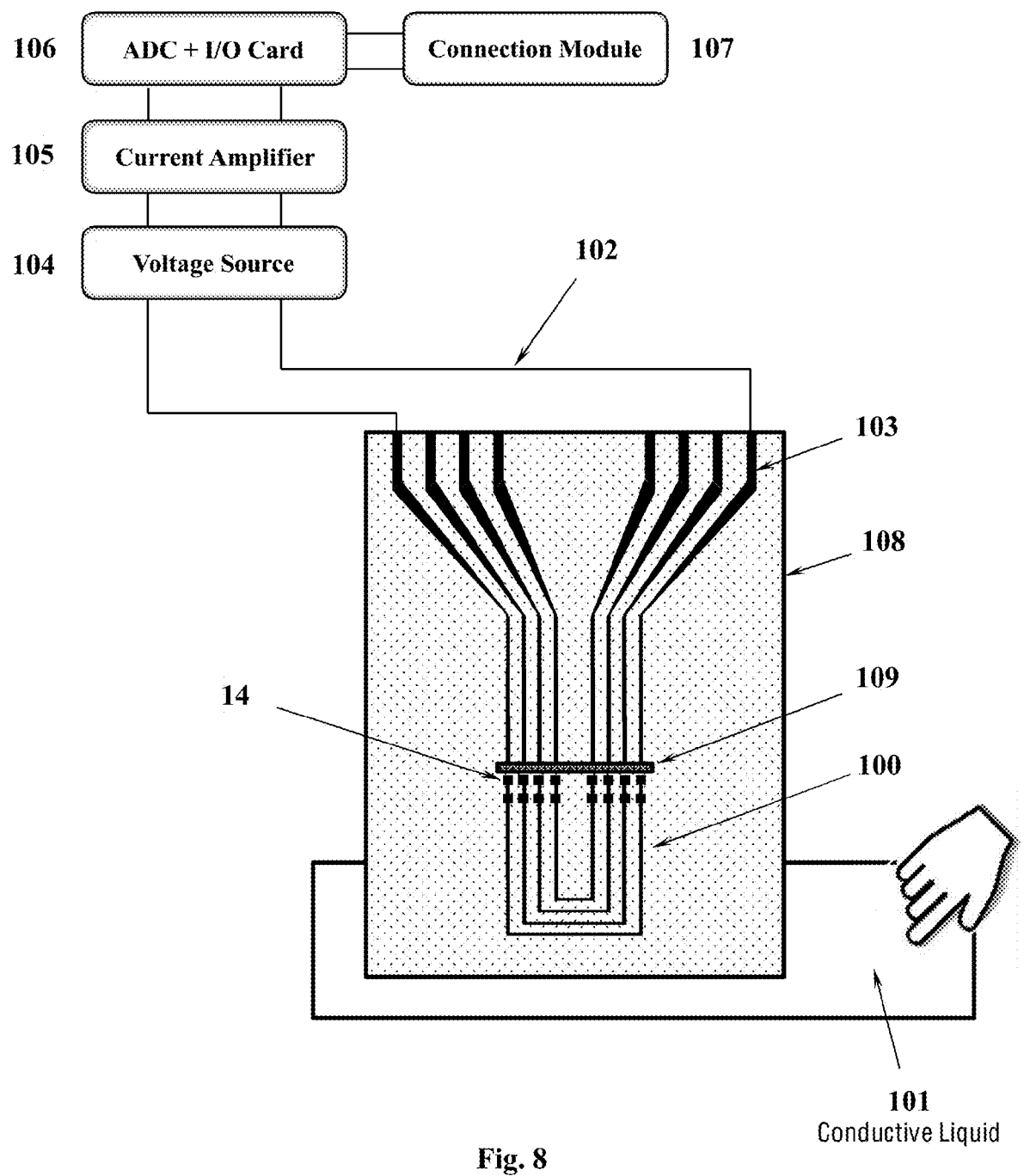
FIG. 8 represents a direct-contact microelectronic sensor of an embodiment.

In another aspect of the present disclosure, FIG. 8 illustrates a microelectronic sensor comprising the following components:
- the PC-HEMT of an embodiment, or an array thereof (100), printed on a flexible printed circuit board (PCB) (108), wherein each one of said transistors is connected via electrical metallizations (14) to its dedicated electrical contact line (103) printed on said PCB (108);
- a voltage source (104) connected to said electrical contact lines (103) via an electric circuit (102) for supplying electric current to said transistors;
- an integrated or CMOS current amplifier (105) connected to said voltage source (104) for amplification of an electric current obtained from said transistors;
- an analogue-to-digital converter (ADC) with in-built digital input/output card (106) connected to said current amplifier (105) for outputting the converted signal to a user interface; and
- a connection module (107) for connecting the sensor to the user interface.

All the above components of the sensor can be external or built in the transistor. As an example, the sensor layout shown on FIG. 8 has an array of four PC-HEMTs for more flexible test procedure. Each PC-HEMT of this sensor is fabricated on the substrate comprising 6-inch silicon wafers, the GaN buffer layer and the ultrathin grown AlGaN barrier layer, as described above. The AlGaN/GaN hetero-junction parameters used in this particular transistor were optimised for the ultrathin AlGaN barrier layer as follows: 3.5 nm SiN cap on top of the barrier layer, 6 nm $Al_{0.25}Ga_{0.75}N$ and 2 µm GaN buffer layer deposited on the Si wafer substrate. All the measurements further exemplified with this sensor were carried out on the fabricated samples without any additional surface treatment after ion implantation based 2DEG patterning step.

For utilisation within the conductive liquid (101), the fabricated sensor is glued on the flexible fibro-plastic PCB (108), and its wire bond connectors are protected with epoxy-based glob-top (109). The voltage source (104) can be any suitable and commercially available battery of the Li-ion type or any energy harvester with AC-DC or DC-DC converters. The ADC card (106) is any suitable analogue-to-digital converter card that can be purchased, for example, from National Instruments® or LabJack®. The current amplifier (105) can be any commercially available femto-ampere amplifier, for example SRS® SR570, DLPVA-100-F-S, FEMTO® current amplifier DDPCA-300 or Texas Instruments® INA826EVM.

Figure 9A:
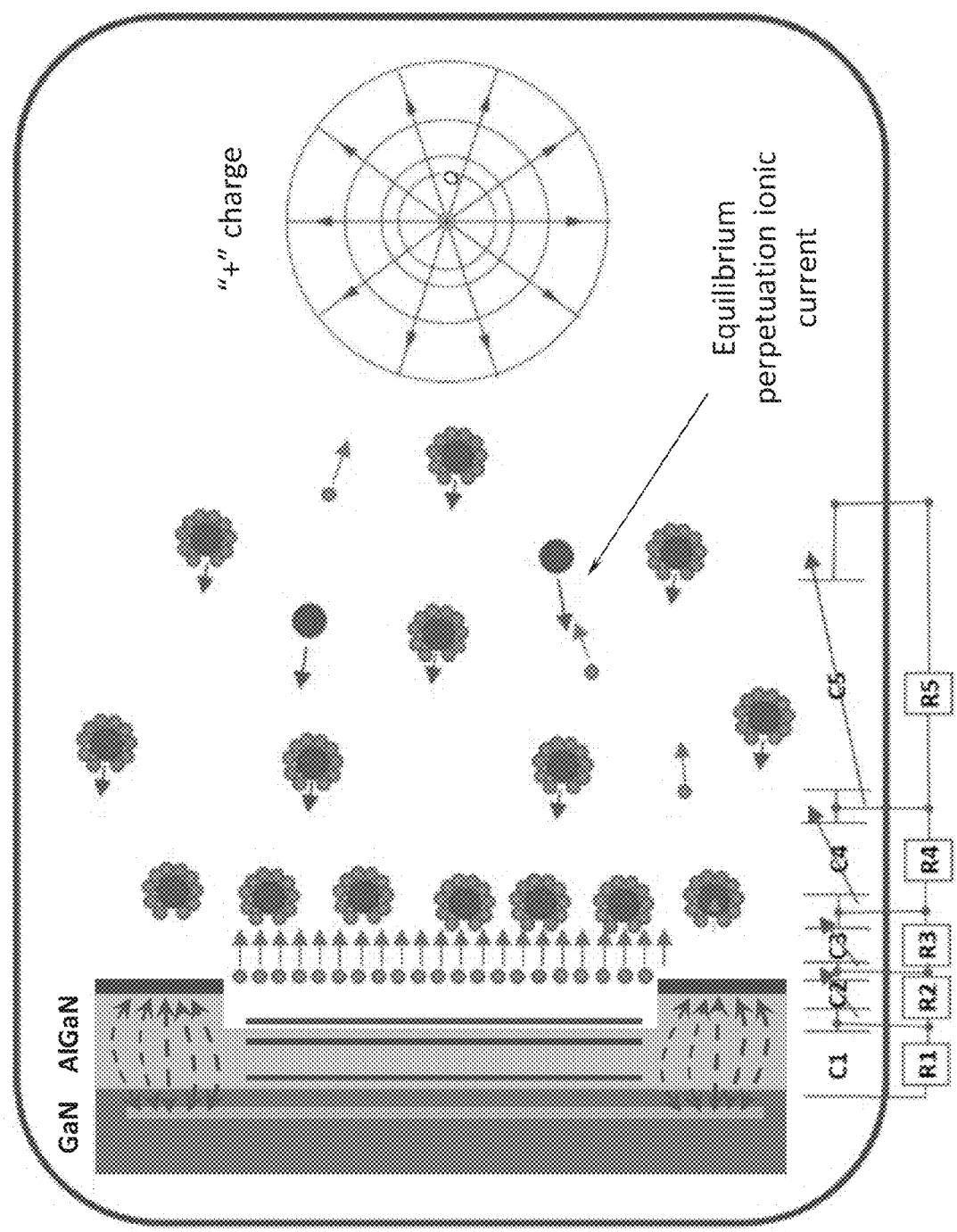
FIG. 9a schematically shows the barrier layer/liquid interface with the double layer formation, simplified equivalent interface circuitry and ion electrodynamics during exposure of the sensor to a positive charge.
Figure 9B:
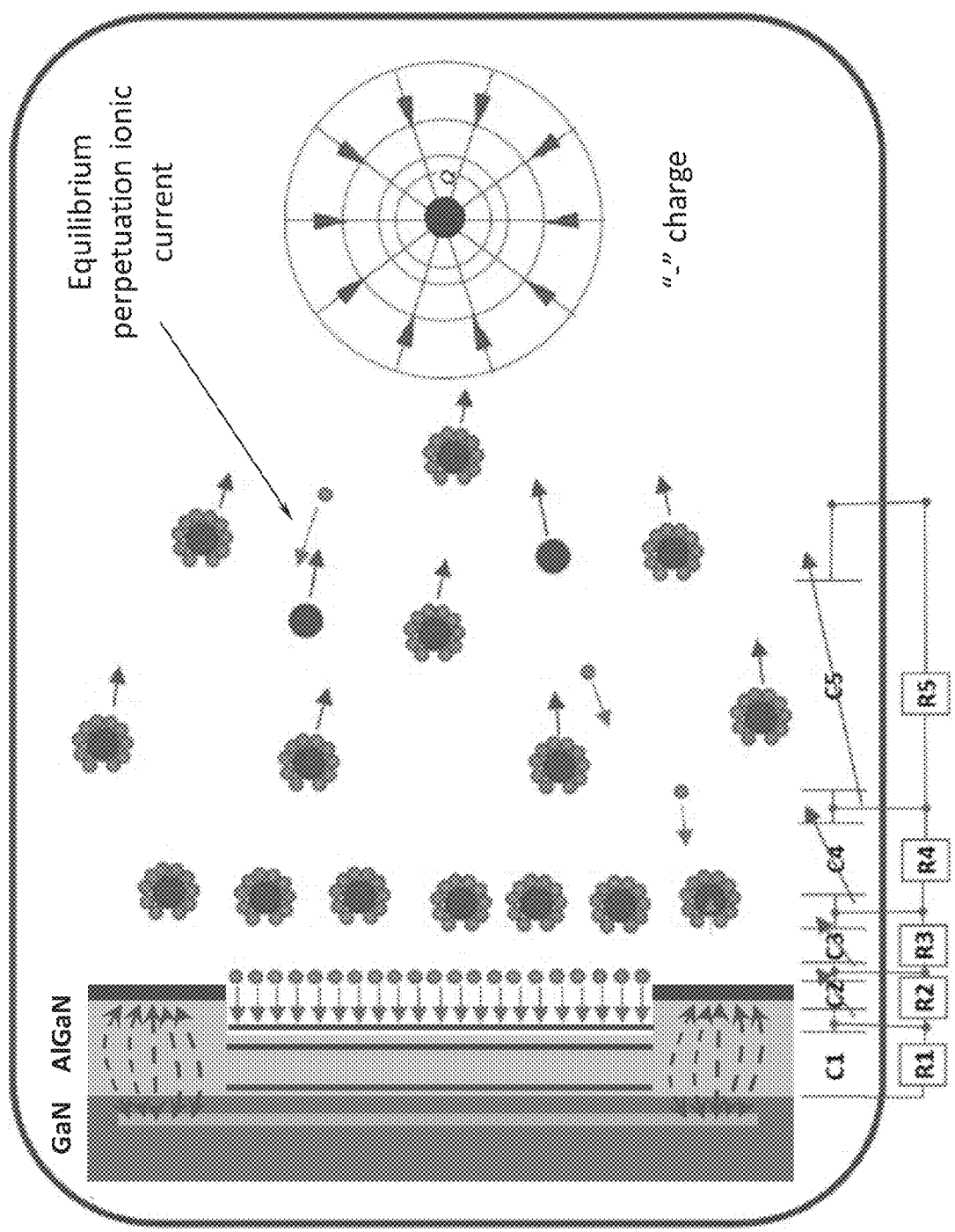
FIG. 9b schematically shows the barrier layer/liquid interface with the double layer formation, simplified equivalent interface circuitry and ion electrodynamics during exposure of the sensor to a negative charge.

In view of the above, the working principle of the PC-HEMT sensor of the present application is based on ultra-high charge sensitivity at the sensor/material/tissue surface interface. FIG. 9 schematically shows the barrier layer/liquid interface with the double layer formation, simplified equivalent interface circuitry and ion electrodynamics during exposure of the sensor to (a) a positive charge and (b) a negative charge. Placed into a liquid, any surface potential causes the natural formation of an electrochemical double layer at the contact interface to maintain charge equilibrium between the solid state and ionic conductive liquid. In FIGS. 9a-9b, this double layer is shown schematically together with the simplified equivalent circuitry at the interface. The double layer is mostly created with a 1-3 nm thick sharp separation between the negative and positive ion space charge zones C2-R2 and C3-R3, which cause a secondary space charge equilibrium zone C4-R4 (10 nm-1 µm) and charge gradient zone C5-R5 disappearing in the bulk liquid. When there is no more potential shift from the solid and from the liquid, then the charge equilibrium is maintained with C1/R1-C5/R5 elements possessing a quasi-constant values.

Ion flow is schematically shown in FIGS. 9a-9b with vector arrows during an electrodynamic rearrangement when an external charge is introduced into an equilibrated electrolyte. FIG. 9a shows the electrodynamic rearrangement with an external positive charge, and FIG. 9b illustrates the electrodynamic rearrangement but with an external negative charge. When the ions react to an external electric field applied in the liquid, the equivalent circuitry mirroring the space charges changes accordingly. Since the sensor of some embodiments of the present application based on the PC-HEMT is extremely sensitive to any surface charge changes (C1/R1), the gradient ions rearrangement in the space charge zones from C5/R5 to a C2/R2 is able to modulate the 2DEG conductivity. The dynamic and magnitude of the new equilibrium is directly proportional to the liquid electrolyte conductivity, ions mobility and external charge value defining the resulted electrolyte charge. In general, any electrolyte strongly enhances the sensor charge response due to the excellent direct charge transfer towards the barrier layer/electrolyte interface. The ions of the liquid interact directly with the super sensitive surface trap states of the ultrathin barrier layer.

Thus, if the sensor is immersed into an ion conductive liquid, then the liquid ions will electro-dynamically react to any external charge by their movement. Being in direct contact to the barrier layer surface, the charge sensitivity is tremendously enhanced. The liquid functions in this case as an antenna perfectly matching to the 2DEG transducer. The heart generates electric charges, and a super position dipole of them is projected to a liquid antenna in which the sensor is immersed in. If the skin surface is in physical contact with the liquid, the detected signal is drastically increased, because the electric field within a body is transferred to the liquid with minimal loses. If the skin surface is outside of the liquid, then the sensed electric field created by the heart polarisation-depolarisation cycle is considerably weaker, but still can be detected by the sensor within 0.1-5.0 m distance from a patient or less, due to its extremely high sensitivity.

As discussed above, at any solid state/electrolyte interface, the capacitive and resistive elements of the sensor form an electrochemical surface potential originated from an interaction between the surface trap states and a double layer capacity, while the interaction between the 2DEG and the surface trap states originates from tunnelling and electrostatics. It has now been surprisingly found that operation of the PC-HEMT sensor as an open gate field-effect transistor is not required in order to modulate the surface electrochemical potential within the barrier layer/electrolyte system.

Figure 10:
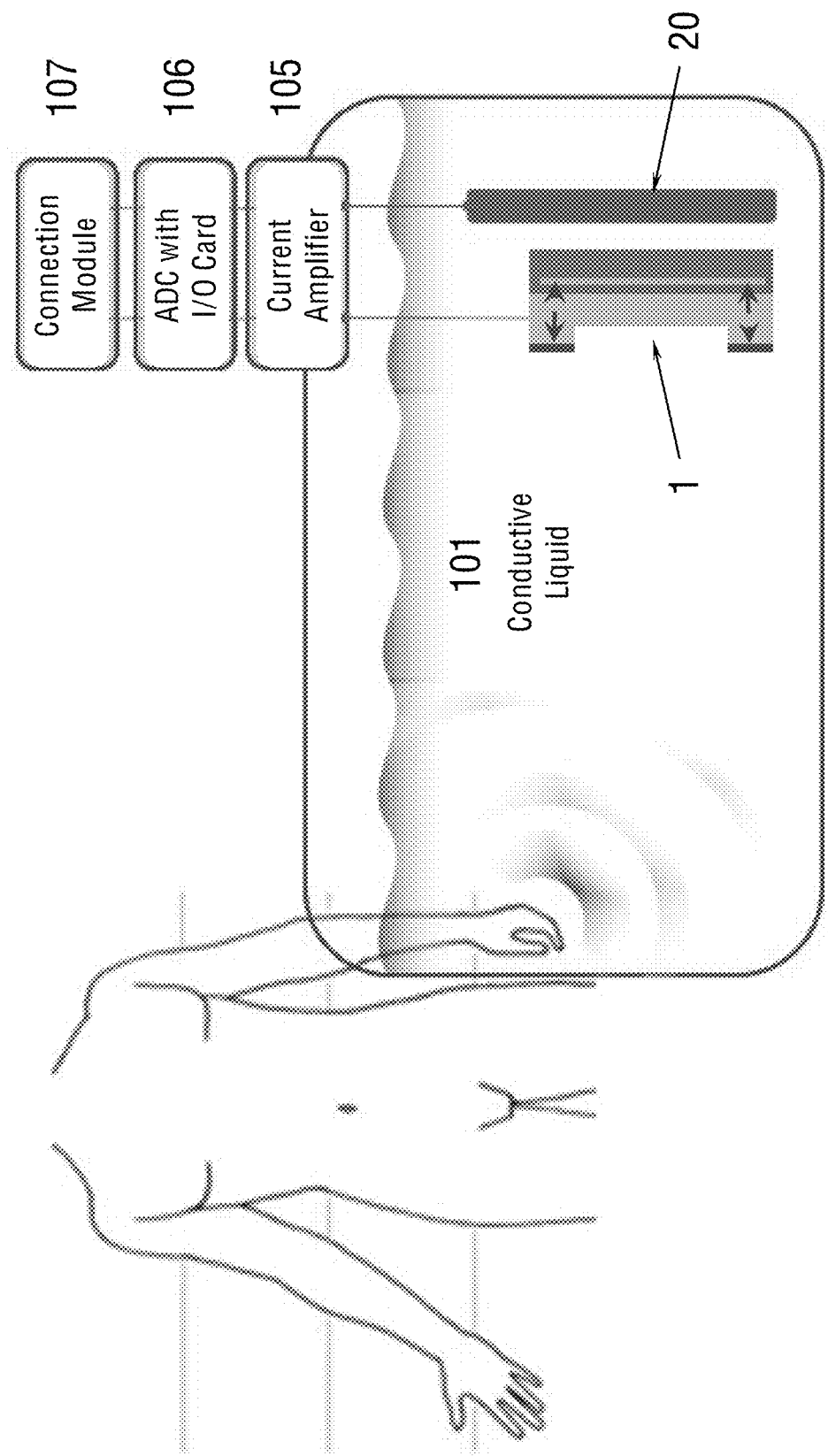
FIG. 10 schematically shows the system of an embodiment based on the PC-HEMT with an Ag/AgCl reference-cell electrode.

For example, in a wired cardio monitoring, the ECG (electrocardiography) electrodes can be attached to a patient's skin and further wired (bridged) with the electrolyte Au or Ag/AgCl gel electrodes. Small electrical resistance of the wires allows transporting the body (or skin) charges into the conductive liquid, where the PC-HEMT sensor is located. In another embodiment, the sensor additionally comprises a reference electrode for remote potentiometric body charge detection. FIG. 10 shows an embodiment of the system of the present application based on the PC-HEMT (1) with an Ag/AgCl reference-cell electrode (20), both dipped into conductive liquid (101) and connected to the readout circuit comprising the discussed above current amplifier (105), analogue-to-digital converter (106) and connection module (107).

Since the C1/R1 component is absent in the equivalent circuitry, there is no quantum mechanical interaction between the surface trap states and 2DEG in this system. Moreover, by definition, AgCl salt, which is non-polarising, cannot change its own potential at surface with ionic exchange processes. This is in contrary to AlGaN surface, which shows strong potential changes when an external charge is introduced in the liquid. While being exposed to the external charge, the response to changing potential at the barrier layer/liquid-interface within the PC-HEMT/liquid/AgCl system can be detected. The distance between the Ag/AgCl electrode and the PC-HEMT does not matter within a relatively compact vessel with the conductive liquid. Example 1 demonstrates the use of this potentiometric system and presents the bio-electrical data recorded with it.

FIG. 11a shows a cross-sectional view of the PC-HEMT configuration of an embodiment with free-standing membranes, comprising:

a multilayer hetero-junction structure made of III-V single-crystalline or polycrystalline semiconductor materials, said structure comprising at least one buffer layer (11) and at least one barrier layer (12), said layers being stacked alternately, and said structure being placed on free-standing membranes (23);

a conducting channel (13) comprising a two-dimensional electron gas (2DEG) or a two-dimensional hole gas (2DHG), formed at the interface between said buffer layer (11) and said barrier layer (12) and providing electron current in said transistor between source and drain contacts;

the source and drain contacts (15) connected to said 2DEG or 2DHG conducting channel (13) and to electrical metallizations (14) for connecting said transistor to an electric circuit; and an open gate area (17) between said source and drain contacts (15);

wherein:
(i) the thickness of a top layer (barrier or buffer) (12) of said structure in said open gate area (17) is 5-9 nm which corresponds to the pseudo-conducting current range between normally-on and normally-off operation mode of the transistor, and
(ii) the surface of said top layer (12) has a roughness of about 0.2 nm or less.

The PC-HEMT shown in FIG. 11a and placed on free standing membranes may be used in "pressure-sensitive" sensors of an embodiment, which are capable of measuring very small pressures. These sensors use the free-standing membranes for creating a mass-loading effect which makes it possible to increase selectivity of the sensors via adding mechanical stress (mass-loading effect) as an additional parameter of the PC-HEMT-based sensor. The free-standing membranes (23) are very flexible free-standing columns of substrate composed of sapphire, silicon, silicon carbide, gallium nitride or aluminium nitride, preferably gallium nitride, having thickness of 0.5-2 μm. The free-standing substrate membranes are very sensitive to any tensile, compressive or mechanical stress changes on the surface of the multilayer hetero-junction structure. This results in a mass loading effect, which will be discussed below.

In general, mechanical sensors, much like pressure sensors, are based on the measurement of the externally induced strain in the heterostructures. The pyroelectric properties of group-III-nitrides, such as gallium nitride (GaN), allow two mechanisms for strain transduction: piezoelectric and piezoresistive. The direct piezoelectric effect is used for dynamical pressure sensing. For measurements of static pressure, such sensors are not suitable due to some leakage of electric charges under the constant conditions. For static operation, the piezoresistive transduction is more preferable.

Piezoresistive sensors using wide band gap materials have been previously employed using hexagonal silicon carbide bulk materials for high temperature operation. Piezoresistivity of GaN and AlGaN structures is comparable to silicon carbide. However, piezoresistivity can be further amplified by HEMT structure, as taught by Eickhoff et al (2001). For piezoresistive strain sensing at relatively lower pressures (or pressure differences), diaphragm or membranes should be used, where the external pressure is transferred into a changed internal strain caused by bending, as shown in FIG. 11b. The resulting change in polarization alters the 2DEG channel current which is measured.

Eickhoff et al (2001) conducted the first experiments on AlGaN/GaN heterostructures where the 2DEG channel confined between the upper GaN and AlGaN barrier layer and demonstrated the linear dependence of the 2DEG channel resistivity on the applied strain. Moreover a direct comparison to cubic SiC and a single AlGaN layer clearly demonstrated the superior piezoresistive properties of the latter. From these results, it is clear that the interaction of piezoelectric and piezoresistive properties improves the sensitivity of pressure sensors by using GaN/AlGaN heterostructures confined with the 2DEG channel.

The sensor configuration schematically shown in FIGS. 11a and 11b involves piezoelectrically coupled, charge and mass sensitive, free-standing GaN membranes, which are prepared, for example, according to U.S. Pat. No. 8,313,968, and offer an elegant and effective solution to achieve both downscaling and an integrated all-electrical low-power sensing-actuation. As mentioned above, GaN exhibits both, piezo- and pyro-electrical properties, which can be functionally combined. Whereas the piezoelectricity enables realisation of an integrated coupling mechanism, the 2DEG additionally delivers a pronounced sensitivity to mechanical stress and charge, which allows the sensor to use the pyroelectric effects. The dynamic change in 2DEG conductivity is also caused by a change in piezoelectric polarisation.

Figure 12:
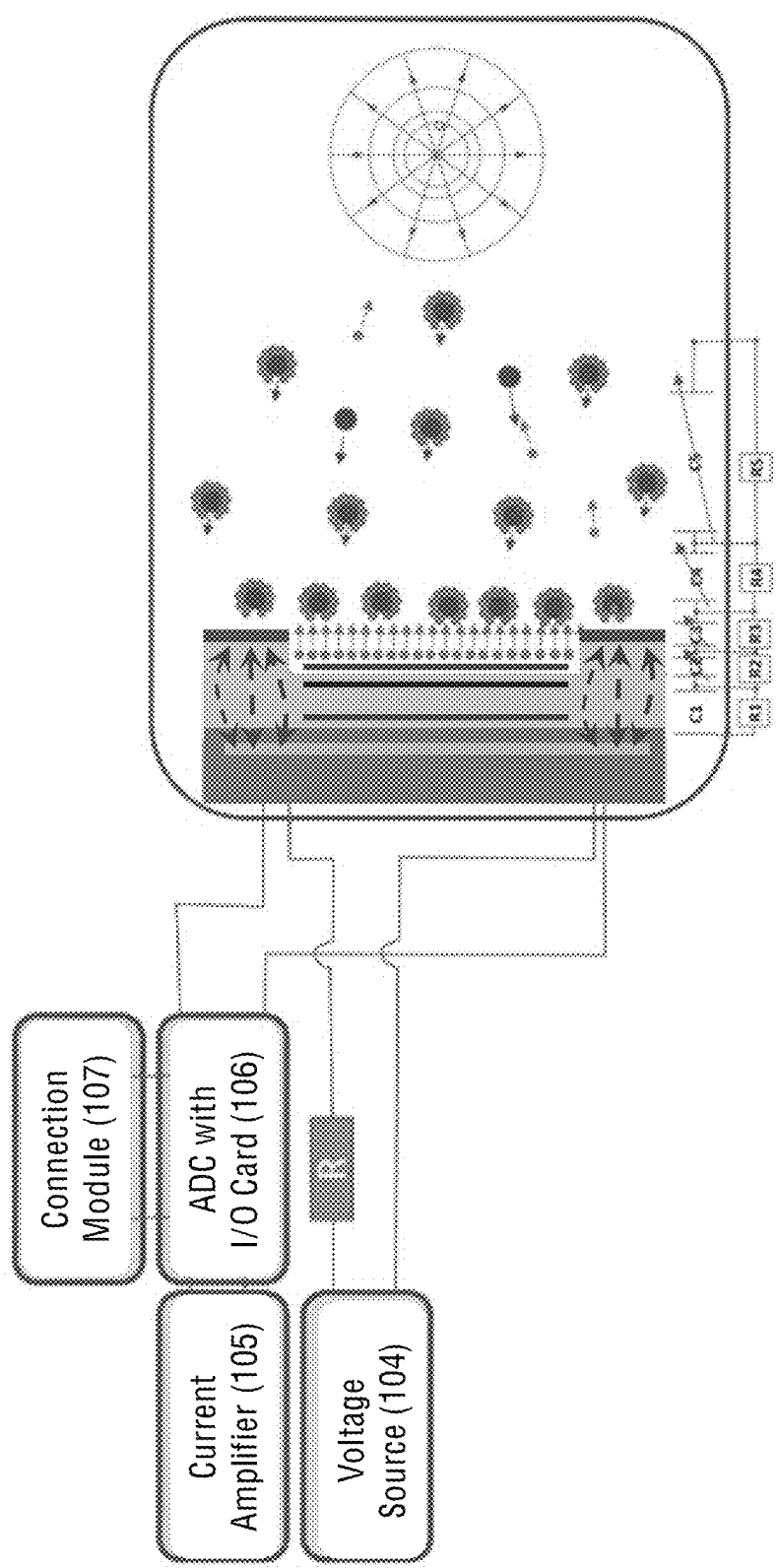
FIG. 12 schematically shows a system of an embodiment, wherein the voltage source is a battery.

In a specific embodiment, the sensor of the present application is powered by a battery. FIG. 12 shows an embodiment of the system of the present application, wherein the voltage source (104) is a battery, for example the AA-battery, which supplies electric current to the PC-HEMT. The setup also includes amplifier (105) with data logger card (106) and connection module (107), such as USB, NFC or Bluetooth. There are two options for setup operation including either differential voltage amplifier (105) connected in parallel, for example SRS® SR560, or a current amplifier (105) connected in-line, for example SRS® SR570. The SR560 setup allows the operation in high input impedance mode using the voltage divider resistance R. The relatively high SR560 input resistance of 100 MΩ is good for detection of very small charges without big leakages.

Another setup includes a current amplifier that operates directly with current flowing via the 2DEG channel of the PC-HEMT into the amplifier with small input resistance of 1MΩ at gain higher than $10^4$ and only 1Ω at gains lower than 200. Since the current amplifier in this case is switched off, the usage of voltage divider R is not necessary unless the voltage of 1.6V from the AA-element is too high. Thus, this setup directly amplifies the electric current modulation in the 2DEG channel originated from an external body charges. All readout components are battery powered to avoid ground loop parasitic current.

Figure 13:
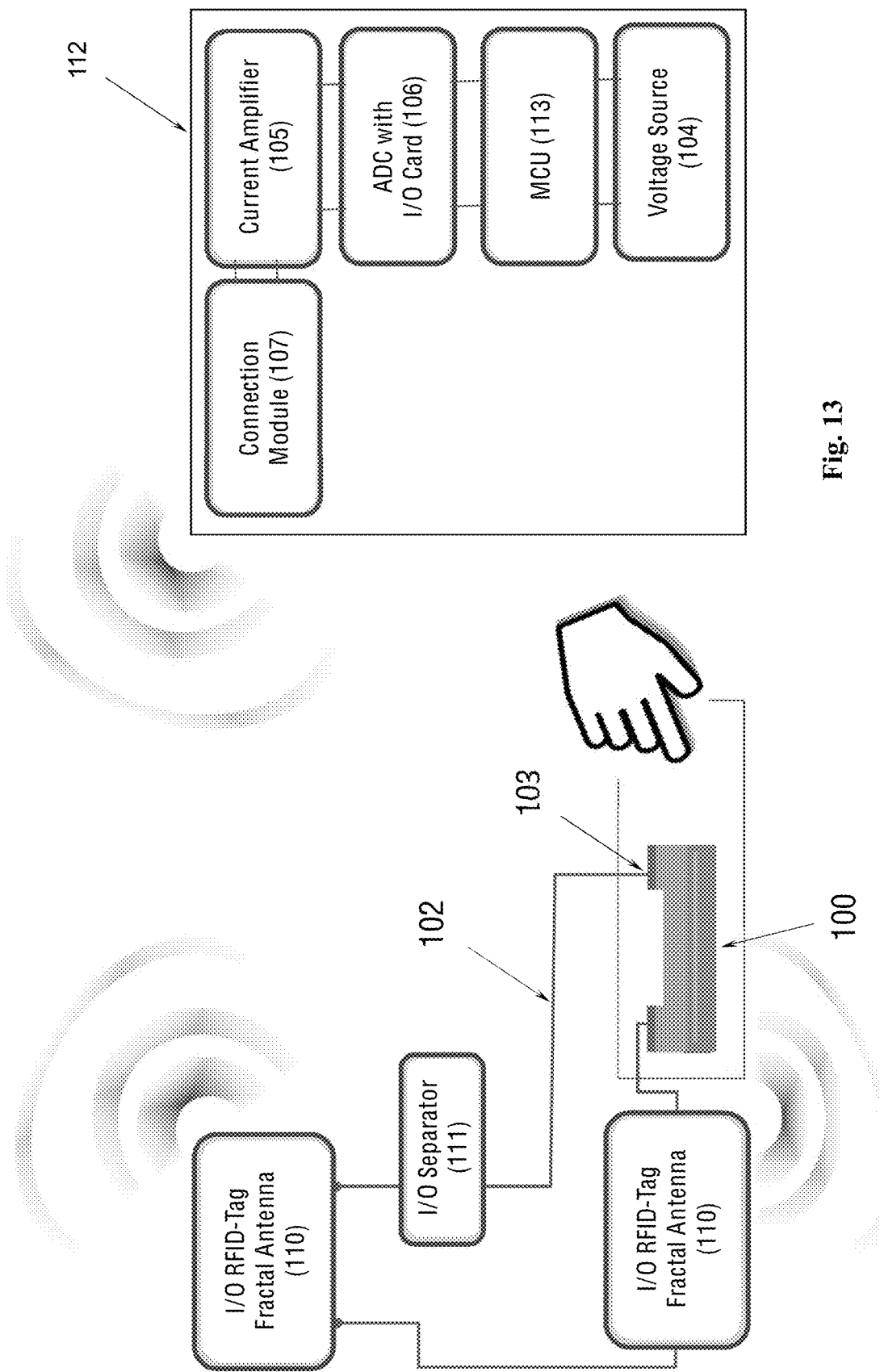
FIG. 13 schematically shows a zero-power RFID sensor of an embodiment with a remote readout.

For the cardiovascular measurements, there are two ways to establish the electrical (galvanic) contact with a patient's body. In a wireless monitoring, the finger can be immersed into an electrolyte solution with the PC-HEMT sensor. The test person and all set up components are electrically isolated to avoid ground loops. Reference is now made to FIG. 13 illustrating a zero-power radio-frequency identification (RFID) sensor of an embodiment of the present application for remote readout. In a particular embodiment, the RFID sensor comprises the following components:

the PC-HEMT of an embodiment, or an array thereof (100), wherein each one of said transistors is connected to its dedicated electrical contact line (103);

one or two out-input RFID-tag zero-power fractal antennas (110), each connected to said electrical contact lines (103) via an electric circuit (102) for receiving or transmitting a signal;

a diode input-output separator (111) to separate polarities in said circuit (102);

an integrated circuit (112) for storing and processing said signal, and for modulating and demodulating a radio-frequency (RF) signals, said circuit comprising:

a) a voltage source (104) supplying electric current to said transistors (100) and to said one or two antennas (110);

b) an integrated or CMOS current amplifier (105) for amplification of an electric current obtained from said transistors (100);

c) an analogue-to-digital converter (ADC) with wireless input/output modules (106) connected to said current amplifier (105) for wireless outputting the converted signal to a user interface;

d) a microcontroller unit (MCU) (113) for processing and converting the received signal into data readable in said user interface; and e) a wireless connection module (107) for wireless connection of said sensor to said user interface.

Figure 14:
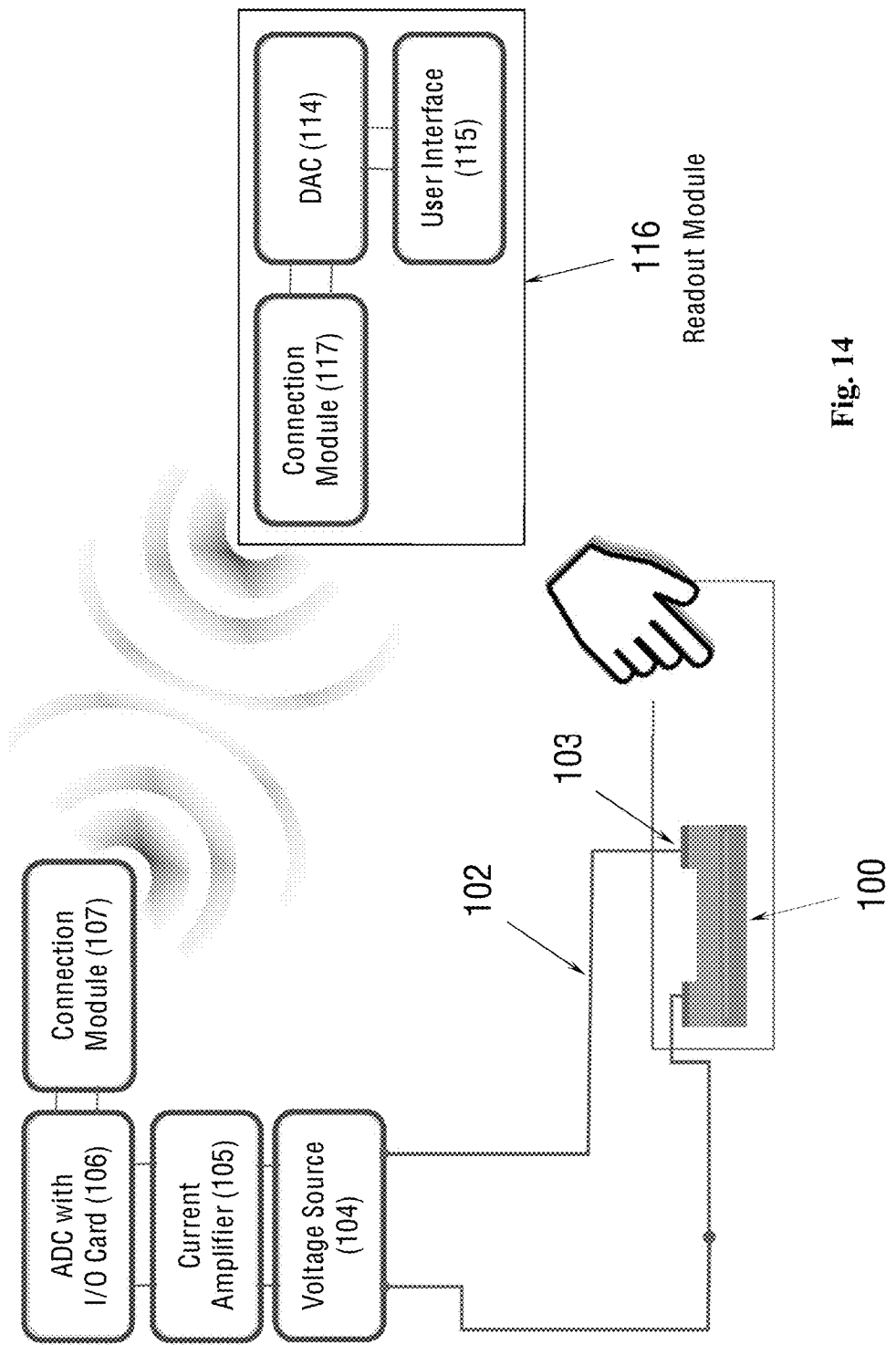
FIG. 14 schematically shows a direct-contact sensor of an embodiment with a remote readout.

The remote readout can be used with any sensor of the present application. In a specific embodiment, FIG. 14 schematically shows a microelectronic sensor of the present application comprising the following components:

the PC-HEMT of an embodiment, or an array thereof (100), wherein each one of said transistors is connected to its dedicated electrical contact line (103);

a voltage source (104) connected to said electrical contact lines (103) via an electric circuit (102) for supplying electric current to said transistors;

an integrated or CMOS current amplifier (105) connected to said voltage source (104) for amplification of an electric current obtained from said transistors;

an analogue-to-digital converter (ADC) with in-built digital input/output card (106) connected to said current amplifier (105) for outputting the converted signal to a user interface (115); and a wireless connection module (107) for wireless connection of the sensor to a readout module (116); wherein said readout module (116) comprises another wireless connection module (117) connecting the sensor to said user interface (115) via a digital-to-analogue converter (DAC) (114).

In some embodiments, both wireless connection modules (107) and (117) are either Bluetooth or NFC, thereby providing wireless communication between the sensor and the readout module for up to 20 m. If these two modules are WiFi, the connection between them can be established for up to 200 nm, while GSM allows the worldwide communication.

Figure 15:
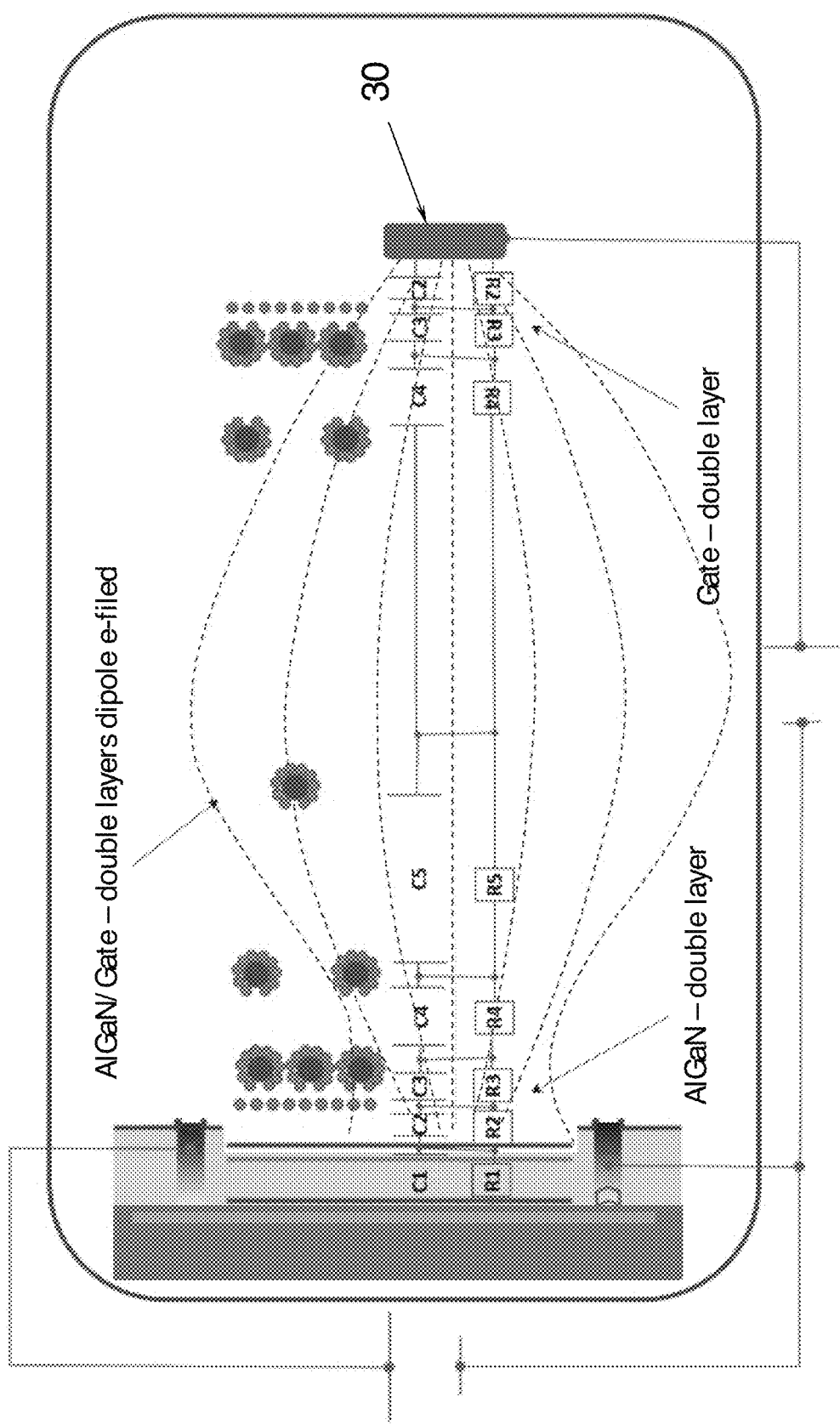
FIG. 15 illustrates the discharging method based on utilisation of the additional liquid gate electrode that is electrically connected to the power source of the sensor.

In yet further embodiment, the sensor of the present application additionally comprises a gate electrode for discharging parasitic electric current. The absence of any connection to a ground for a long time results in a parasitic readout in the system because of tribology effects, through the body friction, through the body charging and finally due to the parasitic charging of the PC-HEMT sensor itself. Since this parasitics has a low energy origin in the surface ionisation processes, it can be neutralised or discharged using an additional gate electrode. The discharging method is based on utilisation of the additional liquid gate electrode that is electrically connected to the power source of the sensor, as illustrated in FIG. 15. A potential difference to the gate electrode in the static liquid is formed, if no additional voltage source is connected to the system. As a result, an electrically coupled field is formed intrinsically affecting the surface charges from the sensor towards the gate electrode double layer. Due to creation of a direct potential difference with an electrical connection between the AlGaN layer surface and the gate electrode, there is much stronger influence on the C1/R1 components inside the AlGaN barrier layer. By applying an additional source-gate voltage through the battery powered signal generator or other power source, the parasitic charges can be de-trapped and neutralised at the AlGaN layer surface.

Figure 16:
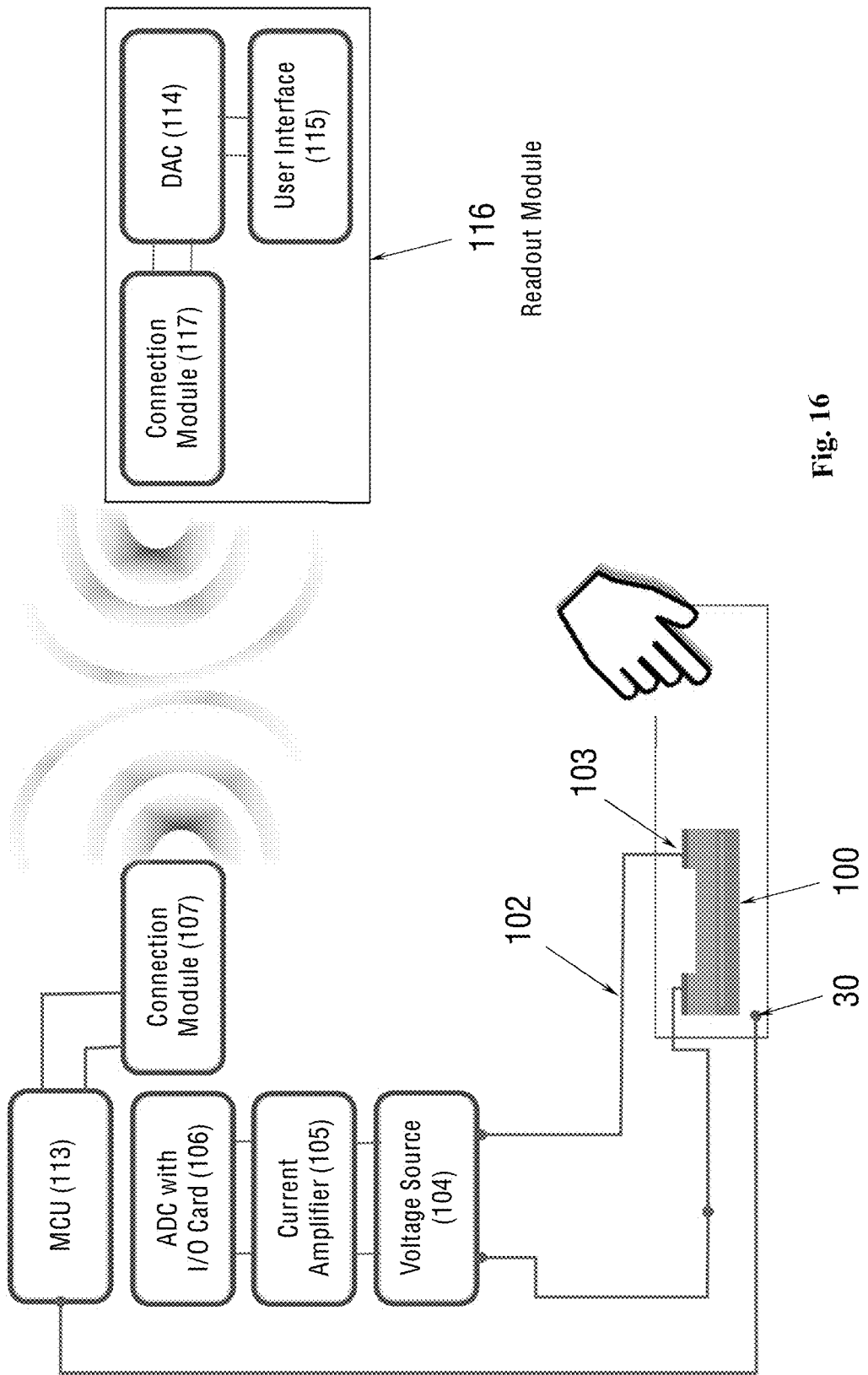
FIG. 16 schematically shows the direct-contact sensor of an embodiment with a remote readout and a feedback control for energy level adjustment and de-trapping via an external or integrated gate electrode.

In yet further embodiment, FIG. 16 schematically shows a microelectronic sensor with a feedback control for energy level adjustment and de-trapping via an external or integrated gate electrode, comprising the following components:

the PC-HEMT of an embodiment, or an array thereof (100), wherein each one of said transistors is connected to its dedicated electrical contact line (103);

a voltage source (104) connected to said electrical contact lines (103) via an electric circuit (102) for supplying electric current to said transistors;

an integrated or CMOS current amplifier (105) connected to said voltage source (104) for amplification of an electric current obtained from said transistors;

an analogue-to-digital converter (ADC) with in-built digital input/output card (106) connected to said current amplifier (105) for outputting the converted signal to a user interface (115);

a feedback control microcontroller unit (MCU) (113) for energy level adjustment and de-trapping via an external or integrated gate electrode (30); and a wireless connection module (107) for wireless connection of the sensor to a readout module (116); wherein said readout module (116) comprises another wireless connection module (117) connecting the sensor to said user interface (115) via a digital-to-analogue converter (DAC) (114).

The gate electrode (30) is made, for example, of the following metal stacks: Cr/Au, Ti/Au, Cr/Al or Ti/W of 5-10/100-300 nm thicknesses, respectively.

Figure 17:
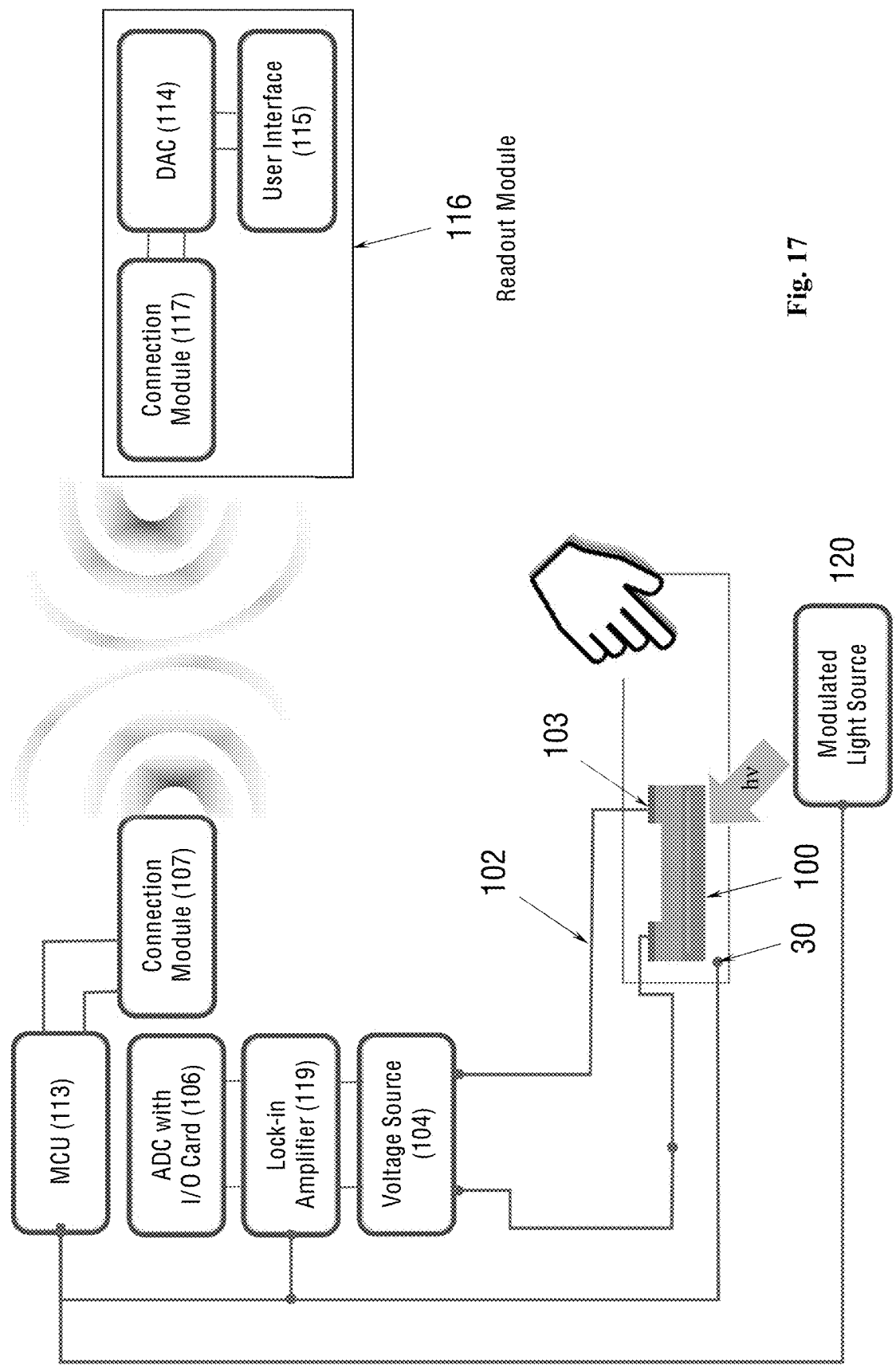
FIG. 17 schematically shows an optoelectronic sensor of an embodiment for remote readout.

In still another embodiment, FIG. 17 schematically shows an optoelectronic sensor of the present application for remote readout comprises the following components:

the PC-HEMT of an embodiment, or an array thereof (100), wherein each one of said transistors is connected to its dedicated electrical contact line (103);

a modulated light source (120), such as a surface-mounted-device light-emitting diode (SMD LED) or UV-VIS-IR laser diode, for irradiating the barrier layer surface of said transistors;

a voltage source (104) connected to said electrical contact lines (103) via an electric circuit (102) for supplying electric current to said transistors;

a lock-in amplifier (119) connected to said voltage source (104) for amplification of a signal with a known carrier wave obtained from said transistors and increasing the signal-to-noise ratio;

an analogue-to-digital converter (ADC) with in-built digital input/output card (106) connected to said lock-in amplifier (119) for outputting the converted signal to a user interface (115);

a feedback control microcontroller unit (MCU) (113) for energy level adjustment and de-trapping via an external or integrated gate electrode (30); and a wireless connection module (107) for wireless connection of the sensor to a readout module (116); wherein said readout module (116) comprises another wireless connection module (117) connecting the sensor to said user interface (115) via a digital-to-analogue converter (DAC) (114).

Figure 18:
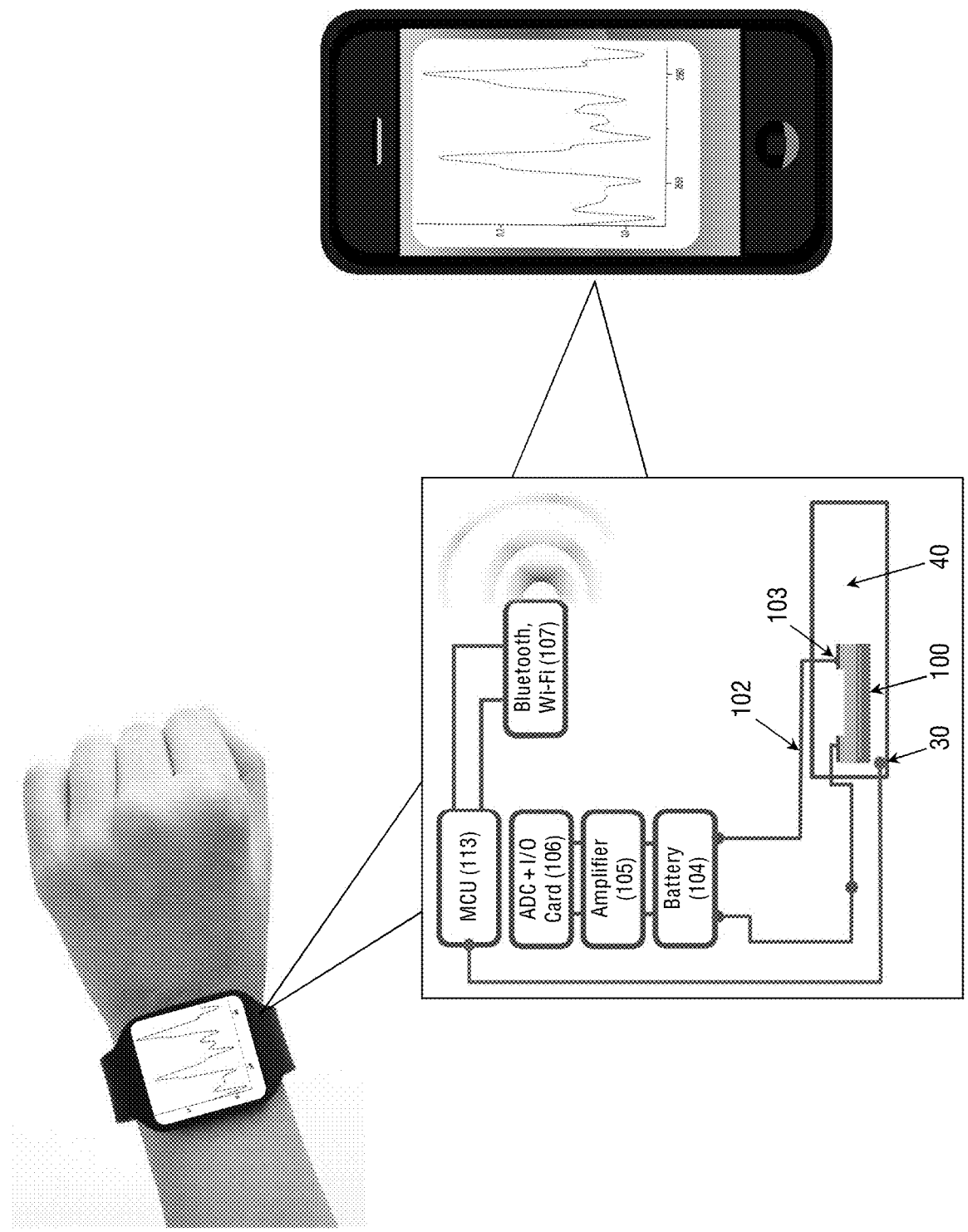
FIG. 18 shows a smart or fitness watch based on the PC-HEMT sensor of the present application according to some embodiments.

FIG. 18 shows a smart or fitness watch based on the PC-HEMT sensor of an embodiment of the present application. The in-built PC-HEMT sensor is capable of sensing the signals and transmitting them either to a phone or directly to a telemedicine cloud. Alternatively, some embodiments of the sensor of the present application can be integrated in a smartphone. The cardiovascular and pulmonary monitoring can be continuously carried out when the phone is in a contact with a hand or activated on calling or when a contact is established. The relevant medical data recorded is then transmitted to a medical-diagnostic telemedicine cloud and will be available for medical doctors.

In a certain aspect, a wearable device of the present application contains an integrated microelectronic sensor comprising the following components:

the PC-HEMT of an embodiment, or an array thereof (100), inserted in an electrolytic contact element (40), wherein each one of said transistors is connected to its dedicated electrical contact line (103);

a battery (104) connected to said electrical contact lines (103) via an electric circuit (102) for supplying electric current to said transistors;

an integrated or CMOS current amplifier (105) connected to said battery (104) for amplification of an electric current obtained from said transistors;

an analogue-to-digital converter (ADC) with in-built digital input/output card (106) connected to said current amplifier (105) for wirelessly outputting the converted signal to a smartphone or to a medical-diagnostic telemedicine cloud;

a microcontroller unit (MCU) (113) for energy level adjustment and de-trapping via an external or integrated gate electrode (30); and a wireless connection module (107) wirelessly connecting said wearable device to a smartphone or to a medical-diagnostic telemedicine cloud.

In a specific embodiment, the wireless connection module (107) can be a short-range Bluetooth or NFC providing wireless communication between the wearable device and a smartphone for up to 20 m. If this module is WiFi, the connection can be established for up to 200 nm, while GSM allows the worldwide communication to a medical-diagnostic telemedicine cloud.

In some embodiments, the wearable device of and the system of the present application can be used for portable long-time-operation solution within a health, fitness and remote telemedicine cloud-based diagnostics. Since the device is used in a continuous cardiovascular and pulmonary monitoring, it should have a very small power consumption saving the battery life for a prolong usage. This is one of the major reasons to use the non-ohmic high-resistive contacts connecting the PC-HEMT sensor to an electric circuit, over the ohmic contacts. The non-ohmic contacts actually limit an electric current flowing through the 2DEG channel by having an electrical resistance 3-4 times higher than the resistance of the 2DEG-channel, thereby reducing electrical power consumption without sacrificing sensitivity and functionality of the sensor. Thus, the use of non-ohmic contacts in some embodiments of the PC-HEMT sensor of the present application is a hardware solution allowing to minimise the power consumption of the device. In another embodiment, the power consumption of the device can be minimised using a software algorithm managing the necessary recording time of the sensor and a battery saver mode, which limits the background data and switches the wireless connection only when it is needed.

EXAMPLES

Example 1: Electric Charge Origin of the Single-Point PC-HEMT Signal

There are different ways for detection of the primary heart activity signal in the beginning of pulse arrival (PAT) cycle within chest, which can be used for blood pressure calculation. The present inventors proved that, in some embodiments, the single-point PC-HEMT signal indeed originates from the heart dipole electric field variations and not from mechanical vibrations of the heart/body.

Figure 19A:
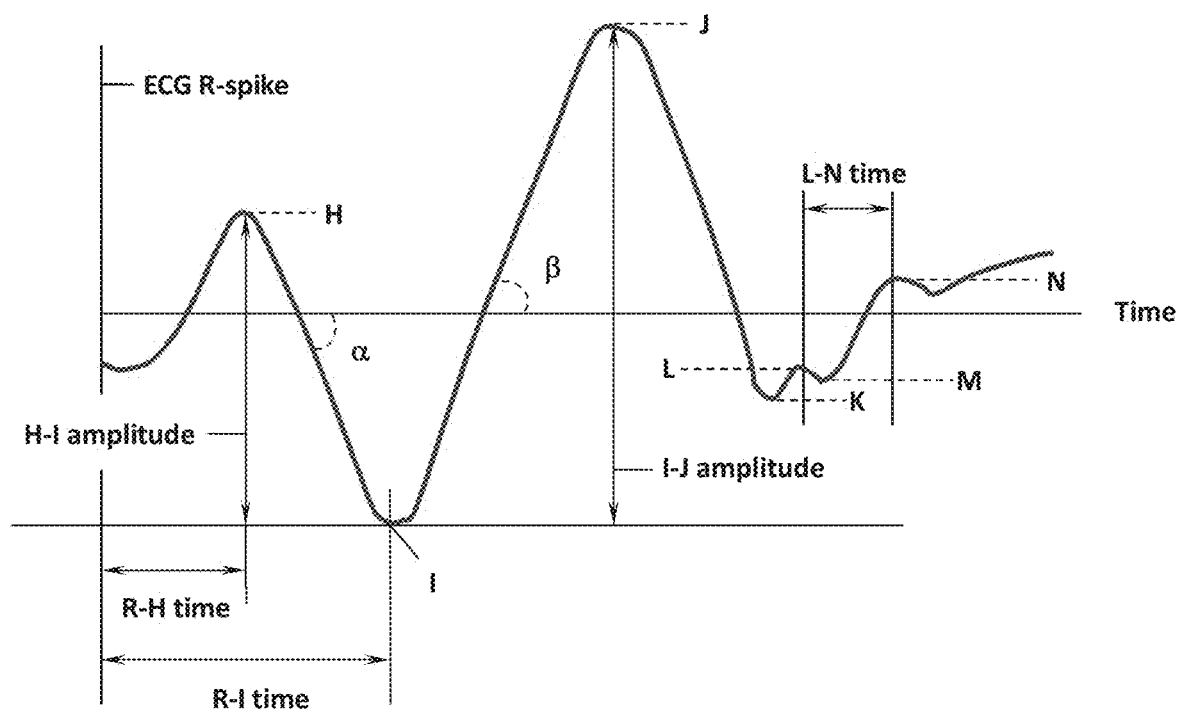
FIG. 19a shows a heart cycle expressed as characteristic ballistocardiography (BCG) peaks.
Figure 19B:
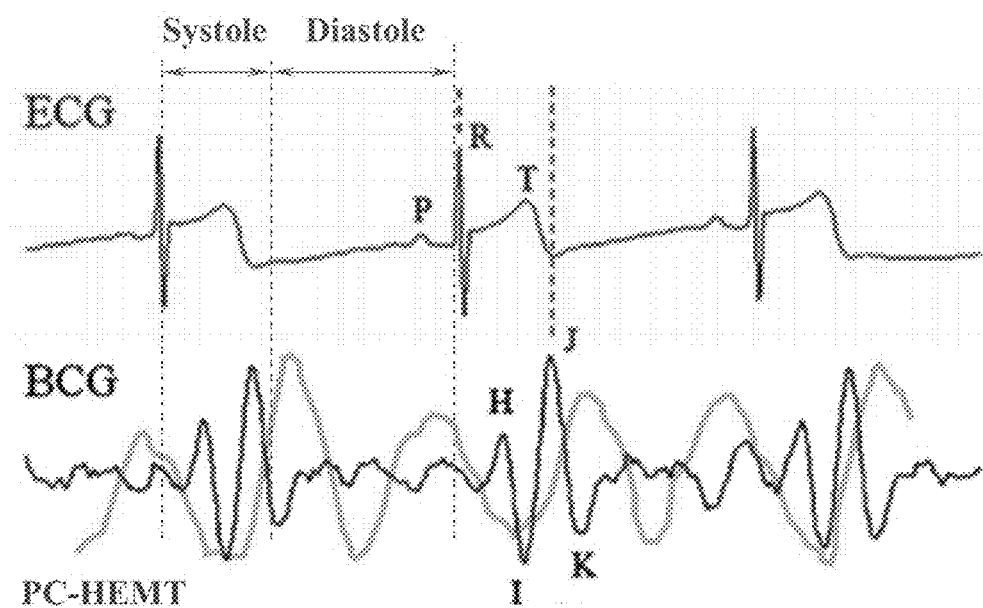
FIG. 19b shows simultaneously recorded ECG and BCG signals with the equivalently time-synchronised PC-HEMT sensor signal (in red).

In the applied biomedical research, the heart vibrations are measured by the technique known as ballistocardiography (BCG of the whole body movements) or seismocardiography (SCG mainly of the thorax movements). The mechanical BCG signal follows the electrical signal with a delay of about 30-40 ms. In the BCG, the mechanical motion of the heart is detected by measuring forces or acceleration from the chest. Alternatively, using the remote BCG recording, the blood pumping activity of the heart can be monitored. A single axis measurement in the length direction of the human body is normally adequate as this is the main direction of the blood flow. FIG. 19*a* shows a heart cycle expressed as characteristic ballistocardiography (BCG) peaks. FIG. 19*b* shows the simultaneously recorded ECG and BCG signals with the entirely (equivalently) time-synchronised PC-HEMT sensor signal (in red).

The wave amplitudes in FIG. 19*a* is a measure of the heart's beat volume, while the time of the peaks' appearance indicates the general functionality of the heart, the heart beat rate and its variability, the latter indicates the recovery state or stress of a person measured. The I and IJ amplitudes of the recorded signals in FIGS. 19*a*-19*b* can be useful in evaluating certain diseases such as aortic valve disease or coronary artery disease, and even in predicting life expectancy. When measuring the BCG signal with an accelerometer, the engineering challenges are the low level of signal acceleration relative to the noise from the sensor and the environment, as well as the frequency response and vibrations of a mechanical setup.

FIG. 19*b* shows a comparison of the time-synchronised ECG, BCG and single-point PC-HEMT sensor measurements. The BCG-signal dynamics of the shown vibrational H-IJK-L-cycle in relation to the P-QRS-T-cycle of the ECG is completely different from the PC-HEMT sensor signal dynamics. The reason for such difference is that the signals obtained from the PC-HEMT originate from dipole charges created by the heart movement and not from its mechanical vibrations. This can be further proven with the PC-HEMT sensor setup shown in FIG. 20, which excludes any mechanical wave transfer.

Figure 20:
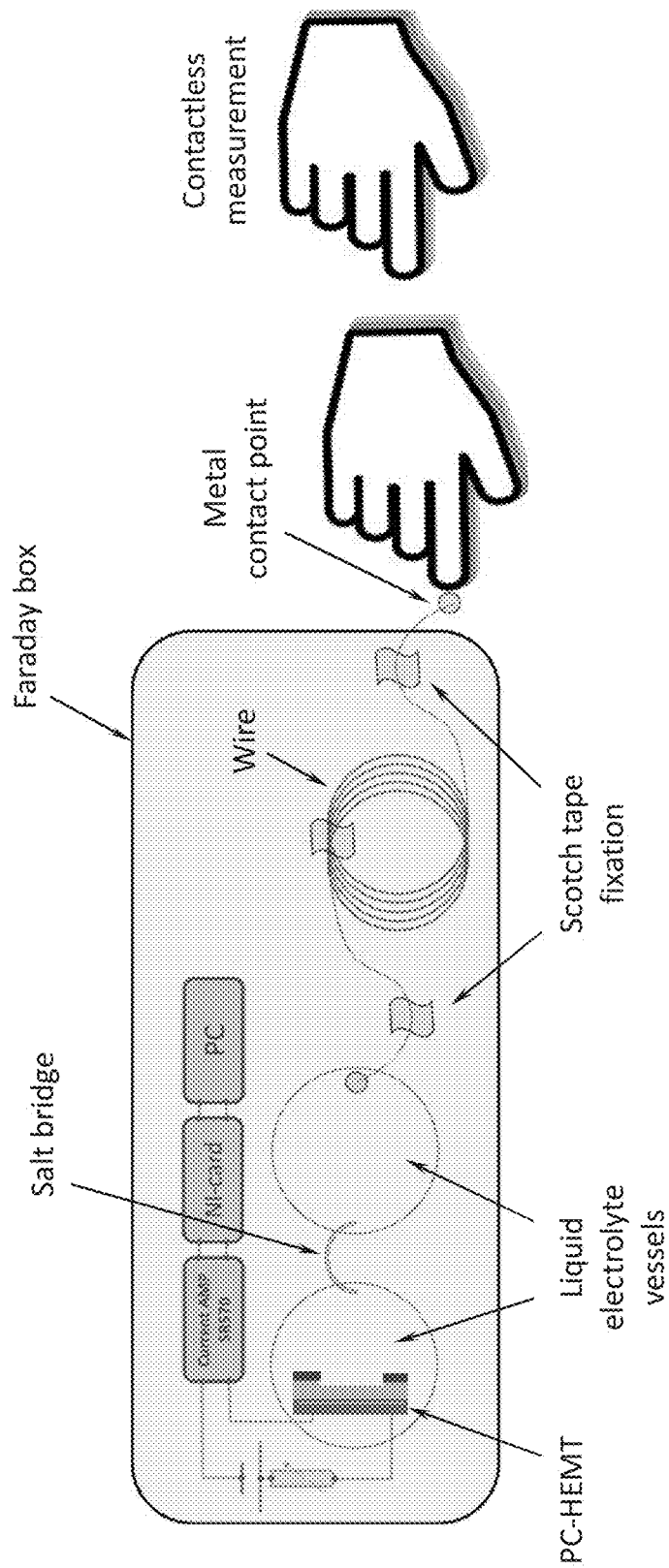
FIG. 20 schematically shows the experimental setup for minimisation of mechanical and vibrational heart movement artifacts.

The sensor setup shown in FIG. 20 is used for minimising the mechanical and vibrational heart movement artefacts, where the PC-HEMT sensor is placed and shielded within a Faraday box. Inside this box, the sensor is placed in a small vessel containing electrolyte saline solution and connected via a salt bridge to another similar vessel with the electrolyte solution. One end of a coiled extension wire was placed in a liquid, while another end was used for contacting a fingertip outside the Faraday box.

The measurements carried without a Faraday box showed the same signal detection. Moreover, the same signal was also detected contactlessly. Thus, the single point monitoring using the PC-HEMT sensor shown in this setup can only be based on the cardiac signals originated from the dipole charges, simply because the transfer of the mechanical vibrations from heart to the sensor is not possible with this particular sensor configuration.

Example 2: Single-Point Measurements in Clinical Tests

Figure 21:
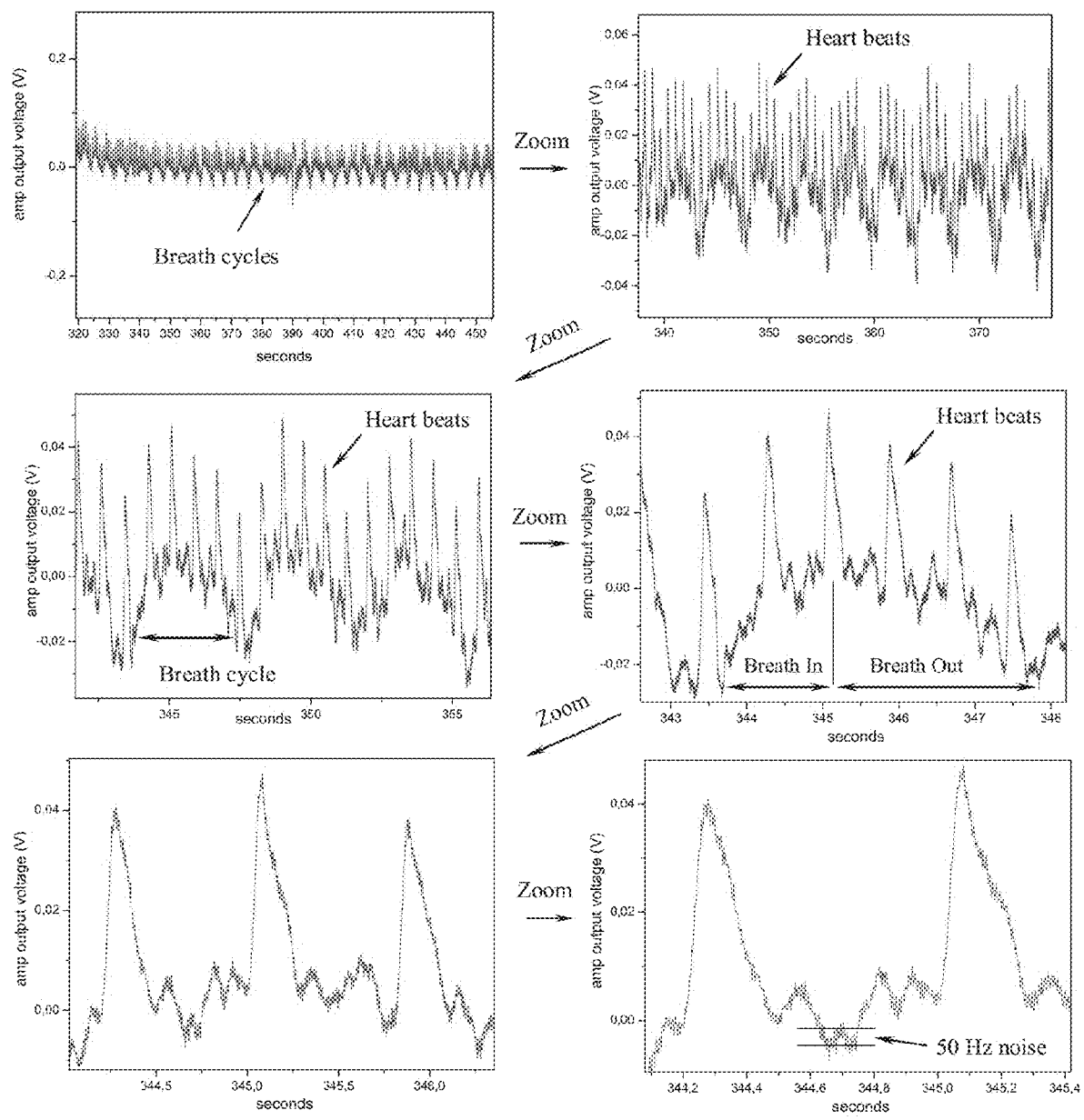
FIG. 21 shows recorded cardiovascular activity at a single body point on the left wrist in zoom-in figures sequence.
Figure 22:
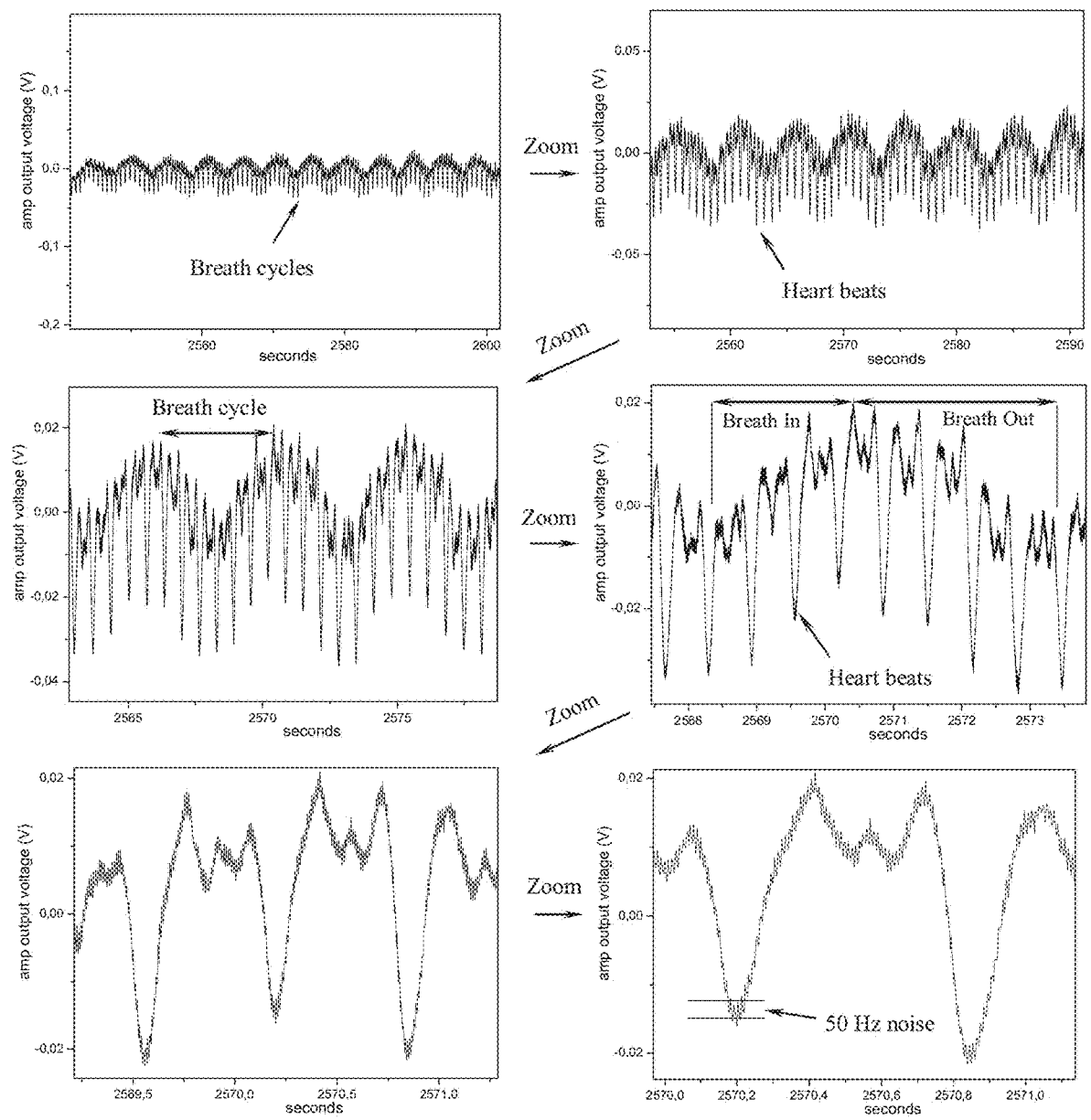
FIG. 22 shows recorded cardiovascular activity at a single body point on the right wrist in zoom-in figures sequence.

The set of single-point measurements in clinical tests has been conducted on a single body point sequentially, first on the left and right wrist positions followed by the measurements on heart, neck and in oral cavity. All the measurements were carried out using current amplifier with a 6 dB bandwidth filter (0.3-30 Hz) and sensitivity (amp factor) of 200 nA/V with input resistance of 10 kOhm. The single body heart signals obtained on the left hand are shown in FIG. 21 in zoom-in figures sequence. The single body heart signals obtained on the right hand are shown in FIG. 22. The signals recorded at both left and right wrists are shape-identical but exhibit opposite polarity due to the natural heart dipole projection in limbs.

Figure 23:
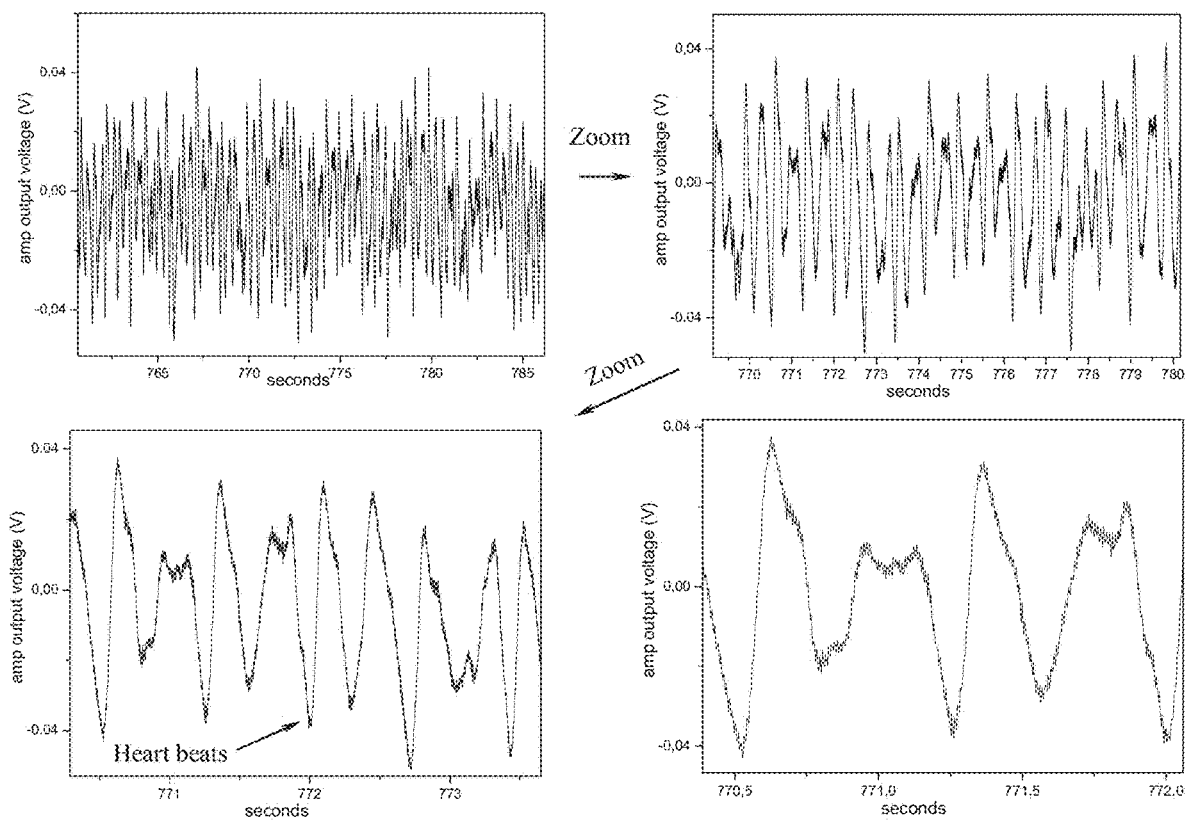
FIG. 23 shows recorded cardiovascular activity measured within oral cavity in zoom-in figures sequence.

FIG. 23 demonstrates the single point heart signals measured within oral cavity in zoom-in figures sequence. During the signal recording inside the oral cavity, the breath oscillations are much smaller compared with wrist signals and the cardiac signal do not anymore exhibit a pronounced upwards or downward orientation of the sharpest heart polarisation cycle peaks.

Example 3: Demonstration of a Huge Intrinsic Amplification Phenomenon

Figure 24A:
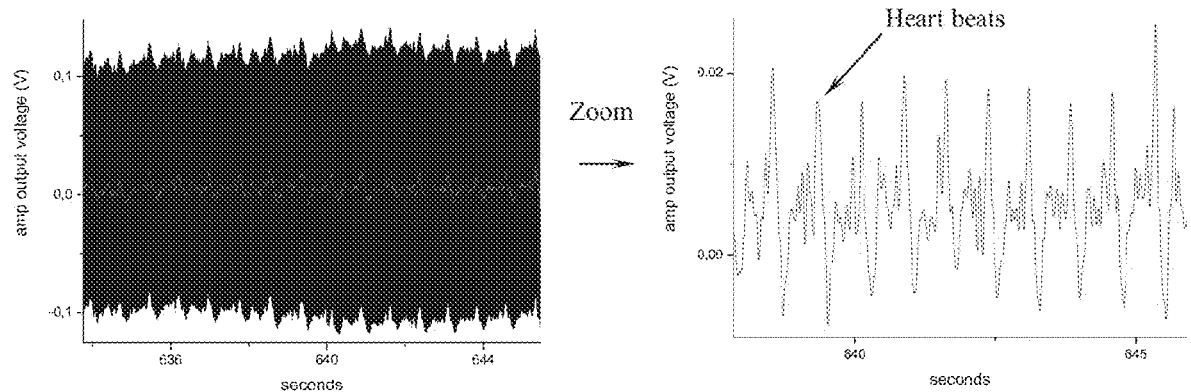
FIG. 24a shows the cardiac signals recorded at a single body point inside the building exposed to a power line of 50 Hz parasitic electromagnetic field. The signals were modulated with 50 Hz noise, in-plane $V_{GS}$=−1.6V and amp gain 500, and plotted after 10 Hz low-pass (LP) filter.
Figure 24B:
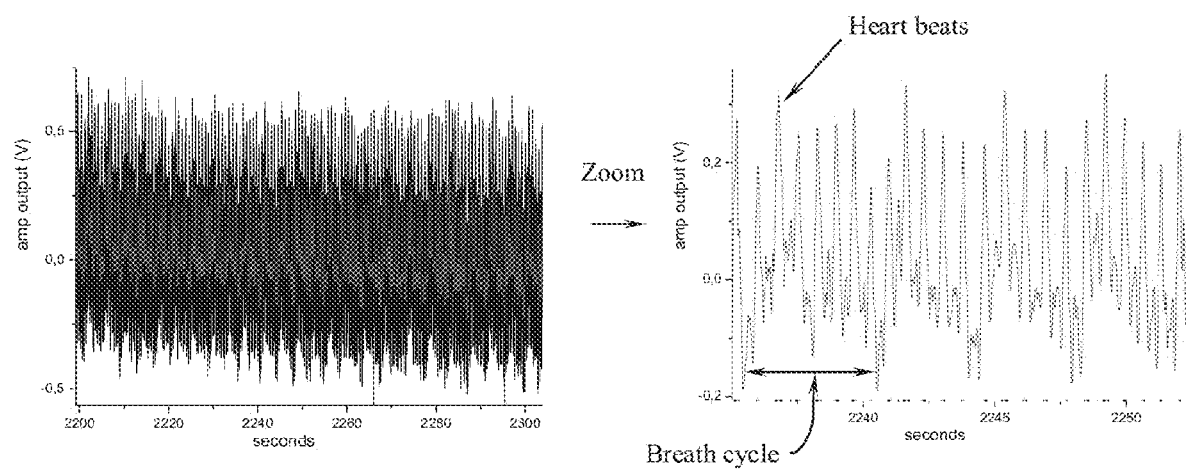
FIG. 24b shows the cardiac recorded at a single body point inside the building exposed to a power line of 50 Hz parasitic electromagnetic field. The signals were modulated with 50 Hz noise, in-plane $V_{GS}$=0V and amp gain 500, and plotted after 10 Hz LP filter.

A series of experiments on increase of the signal stability by means of in-plane gating effect is demonstrated in this example. These experiments show cardiovascular signals well detected indoor in the presence of surrounding 50 Hz noise in Faraday cage protecting the sensor. FIG. 24*a* shows the cardiac signals recorded at a single body point inside the building exposed to a power line of 50 Hz parasitic electromagnetic field. The signals were modulated with 50 Hz noise, in-plane $V_{GS}=-1.6V$ and amp gain 500, and plotted after 10 Hz LP filter. FIG. 24*b* shows the same cardiac signals recorded with 50 Hz noise, in-plane $V_{GS}=0V$ and amp gain 500, and plotted after 10 Hz LP filter.

Thus, despite a strong parasitic 50 Hz noise, it is possible to detect cardiac signals at single body point with rather high signal-to-noise ratio. This parasitic modulation can be easily filtered out using simple (10 Hz-20 Hz low pass) mathematical data processing.

Figure 25A:
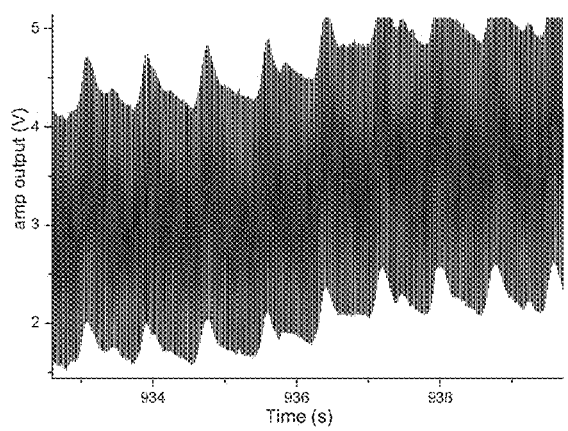
FIG. 25a shows the cardiac signals recorded at a single body point inside the building exposed to a power line of 50 Hz parasitic electromagnetic field. The signals were modulated with 50 Hz noise and amp gain 1000, and plotted after 10 Hz LP filter.
Figure 25B:
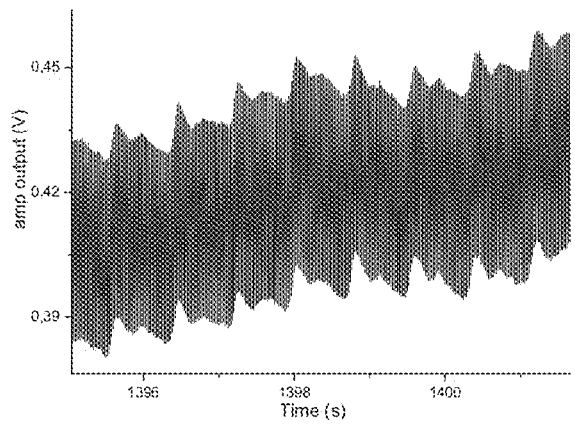
FIG. 25b shows the cardiac signals recorded at a single body point inside the building exposed to a power line of 50 Hz parasitic electromagnetic field. The signals were modulated with 50 Hz noise and zero (0) amp gain, and plotted after 10 Hz LP filter.

A huge intrinsic amplification phenomenon of the PC-HEMT sensor is demonstrated in FIGS. 25*a*-25*b* showing the cardiac signals recorded at a single body point inside the building exposed to a power line of 50 Hz parasitic electromagnetic field. In FIG. 25*a*, the signals were modulated with 50 Hz noise and amp gain 1000, and plotted after 10 Hz LP filter, while in FIG. 25*b*, the amp gain was zero. Thus, such increase in the amplification factor immediately results in the 100% modulation of the sensor current. Since the PC-HEMT signal is tremendously amplified, it is possible to operate the sensor without any additional (external) current amplifier, thereby simplifying an electronic circuit of the sensor and significantly lowering its mass production cost.

While certain features of the present application have been illustrated and described herein, many modifications, substitutions, changes, and equivalents will be apparent to those of ordinary skill in the art. It is, therefore, to be understood that the appended claims are intended to cover all such modifications and changes as fall within the true spirit of the present application.

The invention claimed is:

1. An open-gate pseudo-conductive high-electron mobility transistor comprising:
   (1) a multilayer hetero-junction structure made of gallium nitride (GaN) and aluminium gallium nitride (AlGaN) single-crystalline or polycrystalline semiconductor materials, deposited on a substrate layer or placed on free-standing membranes, said structure comprising at least one buffer layer and at least one barrier layer, said layers being stacked alternately;
   (2) a conducting channel comprising a two-dimensional electron gas (2DEG) or a two-dimensional hole gas (2DHG), formed at an interface between said buffer layer and said barrier layer, and upon applying a bias to said transistor, becoming capable of providing electron or hole current, respectively, in said transistor between source and drain contacts;

(3) the source and drain contacts connected to said 2DEG or 2DHG conducting channel and to electrical metallizations for connecting said transistor to an electric circuit; and (4) an open gate area between said source and drain contacts;

said transistor is characterised in that a thickness of a top layer of said heterojunction structure in the open gate area is 5-9 nanometres (nm) and a surface of said top layer has a roughness of 0.2 nm or less, wherein the combination of said thickness and said roughness of the top layer, upon applying a bias to said transistor, creates a quantum electronic effect of operating said 2DEG or 2DHG channel simultaneously in both normally-on and normally-off operation modes of the channel, thereby making said transistor to conduct electric current through said channel in a quantum well between normally-on and normally-off operation modes of the transistor.

2. The transistor of claim 1, wherein said source and drain contacts are ohmic.

3. The transistor of claim 1, wherein said electrical metallizations are capacitively-coupled to said 2DEG or 2DHG conducting channel for inducing displacement currents, thus resulting in said source and drain contacts being non-ohmic.

4. The transistor of claim 1, further comprising a dielectric layer deposited on top of said multilayer hetero-junction structure.

5. The transistor of claim 1, wherein the thickness of said top layer in the open gate area is 6-7 nm, or 6.2-6.4 nm.

6. The transistor of claim 1, wherein the surface roughness of said top layer in the open gate area is 0.1 nm or less, or 0.05 nm or less.

7. The transistor of claim 5, wherein the surface roughness of said top layer in the open gate area is 0.1 nm or less, or 0.05 nm or less.

8. The transistor of claim 1, wherein said free-standing membranes are free-standing columns of substrate composed of sapphire, silicon, silicon carbide, gallium nitride or aluminium nitride.

9. The transistor of claim 8, wherein said substrate is gallium nitride (GaN) having thickness of 0.5-2 μm.

10. The transistor of claim 1, further comprising an excitation light source for irradiating said structure, thereby inducing an electric current in said 2DEG or 2DHG conducting channel.

11. The transistor of claim 10, wherein said excitation light source is a laser diode or LED.

12. A microelectronic sensor comprising:
the transistor of claim 1, or an array thereof, printed on a flexible printed circuit board (PCB), wherein each one of said transistors is connected to its dedicated electrical contact line printed on said PCB;
a voltage source connected to said electrical contact lines via an electric circuit for supplying electric current to said transistors;
an integrated or complementary metal oxide semiconductor (CMOS) current amplifier connected to said voltage source for amplification of an electric current obtained from said transistors;
an analogue-to-digital converter (ADC) with in-built digital input/output card connected to said current amplifier for outputting the converted signal to a user interface; and
a connection module for connecting said sensor to said user interface.

13. The sensor of claim 12, wherein the connection module is a wireless connection module for wireless connection of said sensor with a readout module, and wherein said readout module comprises another wireless connection module connecting said sensor to a user interface via a digital-to-analogue converter (DAC).

14. The sensor of claim 12, further comprising at least one of: (i) a feedback control microcontroller unit (MCU) for energy level adjustment and de-trapping via an external or integrated gate electrode; (ii) a reference electrode for remote potentiometric body charge detection; or (iii) a gate electrode for discharging parasitic electric current.

15. An optoelectronic sensor comprising:
(1) the transistor of claim 10, or an array thereof, printed on a flexible printed circuit board (PCB), wherein each one of said transistors is connected to its dedicated electrical contact line printed on said PCB;
(2) a voltage source connected to said electrical contact lines via an electric circuit for supplying electric current to said transistors;
(3) a modulated light source for irradiating the barrier layer surface of each one of said transistors;
(4) a lock-in amplifier connected to said voltage source for amplification of a signal with a known carrier wave obtained from said transistors and increasing the signal-to-noise ratio;
(5) an analogue-to-digital converter with in-built digital input/output card connected to said lock-in amplifier for outputting the converted signal to a user interface;
(6) a feedback control microcontroller unit (MCU) for energy level adjustment and de-trapping via an external or integrated gate electrode; and
(7) a wireless connection module for wireless connection of the sensor to a readout module; wherein said readout module comprises another wireless connection module connecting the sensor to said user interface via a digital-to-analogue converter (DAC).

16. A radio-frequency identification (RFID) microelectronic sensor for remote readout comprising:
(1) the transistor of claim 1, or an array thereof, printed on a flexible printed circuit board (PCB), wherein each one of said transistors is connected to its dedicated electrical contact line printed on said PCB;
(2) one or two out-input RFID-tag zero-power fractal antennas, each connected to said electrical contact lines via an electric circuit for receiving or transmitting a signal;
(3) a diode input-output separator to separate polarities in said circuit;
(4) an integrated circuit for storing and processing said signal, and for modulating and demodulating a radio-frequency (RF) signals, said circuit comprising:
(a) a voltage source supplying electric current to said transistors and to said one or two antennas;
(b) an integrated or complementary metal oxide semiconductor (CMOS) current amplifier for amplification of an electric current obtained from said transistors;

(c) an analogue-to-digital converter (ADC) with wireless input/output modules connected to said current amplifier for wireless outputting the converted signal to a user interface;
(d) a microcontroller unit (MCU) for processing and converting the received signal into data readable in said user interface; and
(e) a wireless connection module for wireless connecting of said sensor to said user interface.

17. The sensor of claim 15, further comprising at least one of (i) a reference electrode for remote potentiometric body charge detection or (ii) a gate electrode for discharging parasitic electric current.

18. The sensor of claim 16, further comprising at least one of (i) a reference electrode for remote potentiometric body charge detection or (ii) a gate electrode for discharging parasitic electric current.

19. A wearable device containing an integrated microelectronic sensor, said integrated microelectronic sensor comprising:
the transistor of claim 1, or an array thereof, wherein each one of said transistors is connected to its dedicated electrical contact line;
a battery connected to said electrical contact lines via an electric circuit for supplying electric current to said transistors;
an integrated or CMOS current amplifier connected to said battery for amplification of an electric current obtained from said transistors;
an analogue-to-digital converter (ADC) with in-built digital input/output card connected to said current amplifier for wirelessly outputting the converted signal to a smartphone or to a medical-diagnostic telemedicine cloud;
a microcontroller unit (MCU) for energy level adjustment and de-trapping via an external or integrated gate electrode; and
a wireless connection module for wireless connection of said wearable device to a smartphone or to a medical-diagnostic telemedicine cloud.

20. The transistor of claim 1, wherein said multilayer hetero-junction structure comprises
A. (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have Ga-face polarity, thus forming a two-dimensional hole gas (2DHG) conducting channel in the top GaN layer, close to the interface with said AlGaN barrier layer; or
B. (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have N-face polarity, thus forming a two-dimensional electron gas (2DEG) conducting channel in the top GaN layer, close to the interface with said AlGaN barrier layer; or
C. (i) one top AlGaN layer recessed in an open gate area of the transistor to the thickness of 5-9 nm and having the surface roughness of 0.2 nm or less, and (ii) one bottom GaN buffer layer; said layers have N-face polarity, thus forming a two-dimensional hole gas (2DHG) conducting channel in the GaN buffer layer, close to the interface with said AlGaN barrier layer.

21. A method for manufacturing of the transistor of claim 1, comprising:
a. conducting plasma-enhanced atomic layer deposition (ALD) of alumina ($Al_2O_3$) on a pre-aligned masked Si—GaN/AlGaN wafer with nitrogen-plasma detrapping, thereby creating an Al2O3 layer having thickness of 3-10 nm on the wafer;
b. conducting patterning of the plasma-enhanced ALD of the wafer coated with the $Al_2O_3$ layer in previous step a), with hydrogen fluoride (HF) or with a reactive-ion etching (RIE) technique;
c. conducting patterning of two-dimensional electron gas (2DEG) or two-dimensional hole gas (2DHG) channel of the wafer obtained in previous step b), with argon-ion or nitrogen-ion implantation;
d. conducting plasma-enhanced chemical vapour deposition (CVD) of a dielectric layer over the wafer obtained in previous step c), thereby forming the 2DEG or 2DHG conducting channel areas; and
e. conducting atomic layer etching (ALE) of the wafer obtained in previous step d), thereby removing individual atomic layers from a top of the wafer until the thickness of 5-9 nm of the top layer in the open gate area is achieved, wherein said ALE process allows to maintain the surface roughness of the top layer below 0.2 nm.

* * * * *